United States Patent [19]
Stankov

[11] Patent Number: 5,880,101
[45] Date of Patent: Mar. 9, 1999

[54] CLINICAL USES OF POLYENE MACROLIDES

[75] Inventor: Georgi Stankov, Heimstetten, Germany

[73] Assignee: Dr. Zerle GmbH, Munich, Germany

[21] Appl. No.: 765,616

[22] PCT Filed: Jun. 28, 1995

[86] PCT No.: PCT/EP95/02518

§ 371 Date: Feb. 27, 1997

§ 102(e) Date: Feb. 27, 1997

[87] PCT Pub. No.: WO96/00576

PCT Pub. Date: Jan. 11, 1996

[30]    Foreign Application Priority Data

Jun. 28, 1994 [GB] United Kingdom ............... 9412983
Jun. 28, 1994 [GB] United Kingdom ............... 9412987
Jun. 28, 1994 [GB] United Kingdom ............... 9413010

[51] Int. Cl.⁶ ..................................... A61K 31/70
[52] U.S. Cl. .............. 514/29; 514/31; 514/824; 514/825; 514/838; 514/851; 514/859; 514/861; 514/863; 514/866; 514/877; 514/894; 514/899; 514/903; 514/930; 514/931

[58] Field of Search ............... 514/29, 31, 824, 514/825, 838, 861, 863, 866, 851, 859, 877, 894, 899, 903, 930, 931

[56]              References Cited

U.S. PATENT DOCUMENTS 4,289,757   9/1981   Glenn .................................. 424/120

*Primary Examiner*—Kevin E. Weddington
*Attorney, Agent, or Firm*—Birch, Stewart, Kolasch & Birch, LLP

[57]              ABSTRACT

The present invention relates to the use of at least one polyene macrolide for the preparation of pharmaceutical compositions for the treatment of diseases that are associated with an impaired energy turnover. Particularly, the present inventions allows to specifically stimulate the energy conversion in human cell, i.e. to stimulate the cell metabolism, and thus to treat or prevent a series of diseases.

37 Claims, No Drawings

CLINICAL USES OF POLYENE MACROLIDES

This application is a 371 of PCT/EP95/02518 filed Jun. 28, 1995.

The present invention relates to the use of at least one polyene macrolide for preparing a pharmaceutical composition for the treatment of diseases associated with an impaired energy turnover. The invention particularly allows a targeted stimulation of energy conversion in human cells, i.e., a stimulation of the cell metabolism and thus the treatment or prevention of a variety of diseases.

BACKGROUND OF THE INVENTION

At present more than 200 different polyene macrolide antibiotics have been described, most of them being produced by soil actinomycetes, mainly by the genus Streptomyces.

Polyene macrolides (referred to in the following also as polyenes or macrolides) are characterized by 20- to 40-membered lactone rings containing three to eight conjugated carbon-carbon double bonds. Often, the lactone ring carries a sugar moiety. Some macrolides contain an aliphatic side chain, optionally carrying an aromatic substituent. Usually, the macrolide ring carries at least one hydroxyl group.

Nystatin was the first substance from the class of the polyene macrolides to be described. In 1961 it was isolated as the metabolite of the fungus species *Streptomyces noursei*. Nystatin, referred to in the following as Nys, has the following structural formula:

Although particularly Nys and Amp have been known for several decades and have been administered orally to millions of patients, their therapeutical use has been limited exclusively to the treatment of candidiases (mycoses). In vitro studies have shown that Nys and Amp administered in decreasing dosages may have fungicidal, fungistatic or mycotic growth enhancing effect. Most scientific publications are quite silent about the latter effect. In turn, there are many in vivo studies which found cell-stimulating effects of Nys and Amp in eucaryotic cells (J. Bolard, How do polyene macrolide antibiotics affect the cellular membrane properties, Biochim. Biophys. Acta (1986), 864, 257–304).

It is assumed in the art that the antimycotic effect of Nys and Amp is based on a specific interaction with the membrane-bound ergosterol of the fungi. This interaction is believed to effect disruption of the fungal membranes, the entry of ions and other soluble substances in the fungi, thereby inhibiting the fungal metabolism and bringing about lysis of the fungal cells. It will be shown in the present invention that this conventional concept is not capable of explaining the manifold pharmacological effects of the polyene macrolides. The wrong pharmacodynamic concept, on which the practical use of this class of substances has so far been based, only can give an explanation for the fact that the universal therapeutical potential of polyene macrolides so far has not be recognized.

In the art, Nys and Amp are only used in the therapy of superficial and gastrointestinal mycotic infections. For example, for the treatment of intestinal candidiases and monoliases the administration of Nys in a dose of $3-4 \times 10^6$ I.U./day over a period of 8 days, followed by a dose of 1.5 to $2 \times 10^6$ I.U./day in the following 8 days is recommended.

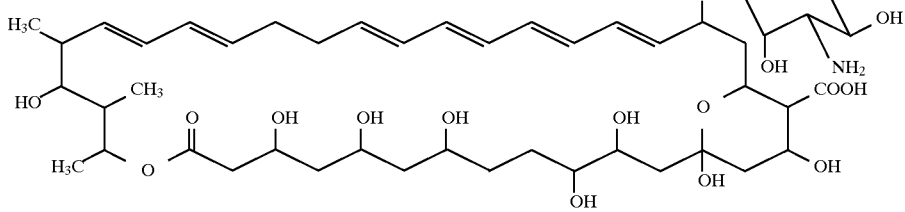

Due to its π-electron structure comprising 4 conjugated double bonds, Nys is referred to as tetraene macrolide.

Another example of a polyene macrolide is Amphotericin B (referred to in the following as Amp). In contrast to Nys, this compound has an additional double bond. Since Amp exhibits a total of seven conjugated double bonds, it is classified among the group of the heptaene macrolides. Amp has the following structural formula:

For the treatment of mycotic infections of the skin, e.g., application of a Nystatin cream ($1 \times 10^5$ I.U./g ointment) 2 to 3 times a day until remission of the infection (about 6 days) is recommended. 1 g Nys corresponds to about $5 \times 10^6$ I.U. The oral and topical dosages, however, which are recommended in the art and are usually administered, are far lower and/or the duration of the treatment is considerably shorter than the dosage or duration of the therapy recommended by the present invention for the indications described in the

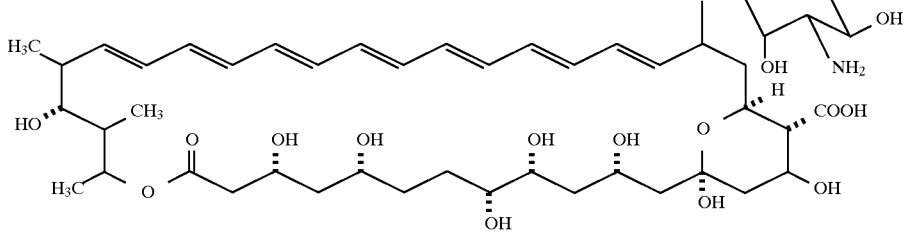

invention. This may further explain why the new therapeutical effects of the polyene macrolides have not been recognized so far.

Additionally, there is the general assumption, which, however, is not verified by scientific findings, that polyene macrolides, such as Nys and Amp, are not or only insufficiently resorbed in the gastrointestinal tract upon oral, intranasal or topical administration (e.g., Van den Boussche, H. et al., CRC Crit. Rev. Microbiol. (1987), Vol. 15, 57–72; Arzneimittel Fortschritte 1972–1985, Kleeman et al. Eds., Verlag Chemie, Weinheim, Germany, 1176–1184; Goodman & Geiman's, The Pharmacological Basis of Therapeutics, (1992), $8^{th}$ edition, Vol. 2, page 1178). This prejudice must be regarded as the main reason why the practical use of Nys has been limited to the local treatment of candidiases and why a possible systemic use has not been recognized.

There is yet another reason for the limited use of polyene macrolides in the art. It is known that Nys and all other polyenes are substantially toxic when administered intravenously or intramuscularly. Upon i.m. injection, severe local inflammations are observed. Upon i.v. administration, renal injuries as well as other severe side effects can occur. Therefore, Nys is not admitted for i.v. therapy. Amp, which is admitted for i.v. therapy, although it is even more toxic when administered in vitro and in vivo than Nys, may be administered only in doses that are 20- to 100-fold lower than the oral doses.

The practical experiences which were made world-wide with the oral therapy in millions of patients with Nys and Amp furthermore show that these substances are well-tolerated. Apart from a mild, temporary sickness in the beginning of the therapy, which occurs in less than 1% of patients and quickly abates, no severe side effects are so far known. This is evident from a literature search which evaluated about 2,000 publications dealing with this topic. This discrepancy—high toxicity upon i.v. and i.m. administration on the one hand and no toxicity upon oral administration on the other hand—has additionally reinforced the general prejudice that polyene macrolides are not resorbed.

SUMMARY OF THE INVENTION

It is therefore the problem underlying the present invention to broaden the therapeutical spectrum of polyene macrolides.

This problem was solved starting from a surprising finding, namely that polyene macrolides, their pharmaceutically acceptable salts and functional derivatives can be used to treat diseases the origin and course of which are associated with an impairment of energy conversion, i.e., the energy turnover, of body cells of mammalians, particularly of humans.

In contrast to other macrolide compounds the polyene macrolides used according to the invention improve the cellular energy turnover by modulating the frequency of cellular potential fluctuations, thereby effecting a remission of the symptoms of the disease.

The active ingredients used according to the invention possess an elongated, sometimes rod-shaped structure. The length can be about in the range of the thickness of the lipid bilayer of biological membranes (about $20 \times 10^{-10}$ m). The elongated, rod-shaped macrolide ring preferably has a longitudinal side that is more hydrophobic and another that is more hydrophilic. The hydrophobic side is made up from a polyene chain from a variety of completely or partially conjugated carbon-carbon double bonds that are preferably in the trans-position to each other The hydrophilic part is formed by a usually mainly $sp^3$-hybridized carbon chain which carries at least one more hydrophilic substituent, such as a hydroxyl group. Individual, i.e., one or two, carbonyl groups and/or C=C bonds can also be contained in the more hydrophilic side. As another structural element the compounds may have at one end of the rod-shaped structure an amino sugar moiety, particularly a mycosamine or a perosamine moiety, and optionally a carboxyl group. At the other end of the rod there is often at least one polar hydroxyl or carbonyl group.

The preferred polyene macrolides according to the invention are characterized by a dipole structure which in terms of its functionality is very similar to that of integral membrane proteins. The preferred macrolides possess a dipole energy $E_D$ of about $10^{-19}$ J, such as about 1 to $2.5 \times 10^{-19}$ J in the electric field of the cellular plasma membrane potential based on the following approximation formula for calculating $E_D$:

$$E_D = n.e.l.F_p$$

wherein n is the number of non-aromatic $\pi$-electrons from C=C bonds on the more hydrophobic part of the macrolide ring, e is the charge of an electron ($1.6 \times 10^{-19}$ coulomb, l is the length of the $\pi$-electron chain and $F_p$ is the electric field strength of the plasma potential of a body cell ($4.5 \times 10^7$ $Vm^{-1}$). For example, for Nys n=12 and l=$22 \times 10^{-10}$ m. Based on these data an $E_D$ value of about $1.9 \times 10^{-19}$ J is calculated. For Amp an $E_D$ value of about $2.2 \times 10^{-19}$ J is calculated.

All macrolides used according to the invention promote the energy turnover E of the cells by increasing the frequency f of the cellular action potential according to the formula $E=E_A.f$, wherein $E_A$ represents the constant energy of an action potential.

The problem is particularly solved by polyene macrolides having 4 to 7 conjugated carbon-carbon double bonds, preferably in the trans position, as well as by their functional derivatives.

For the indications according to the invention, the macrolide compounds are administered orally, topically or intranasally.

Suitable functional derivatives of polyene macrolides are compounds in which at least one hydroxyl and/or carboxyl group of the macrolide is derived to give an ester function, without substantially modifying the cell-stimulating effect of the polyene. Examples of suitable esters comprise $C_1$–$C_5$ alkyl esters. Further suitable functional derivatives comprise N— $C_1$–$C_5$ alkyl derivatives of amino group containing macrolides having cell stimulating activity. Within the scope of the invention, $C_1$–$C_5$ alkyl comprises methyl, ethyl, n- and i-propyl, n-, i- and t-butyl or n-, i- or neopentyl; methyl and ethyl are particularly preferred. Pharmaceutically acceptable salts comprise conventional acid addition salts as well as alkali and alkaline earth metal salts, if amino or carboxyl groups are present in the polyene macrolides.

Examples of polyene macrolides having 4 to 7 conjugated double bonds which are useful according to the invention can be seen in the attached Tables 1 to 4. A particularly preferred group of polyene macrolides useful in the invention comprises compounds of amphoteric nature, particularly those compounds having an amino sugar moiety according to the above definition and a carboxyl group at the same end of the elongated macrolide structure.

According to the invention, it is particularly preferred to use Nys or Amp and their functional derivatives as well as those polyene macrolides according to the above general definition which have a spectrum of activity which is essentially comparable with that of Nys and/or Amp. However, in order to achieve the purpose according to the invention it is by no means necessary that the polyene macrolide used is absolutely identical with Nys and Amp as regards its functionality. The problem underlying the invention is also solved in that the polyene macrolide selected possesses only part of the novel therapeutical effect described in the experimental part for Nys and Amp.

Further representatives of the tetraene, pentaene, hexaene and heptaene macrolides useful according to the invention, and microorganisms producing these compounds are described in Macrolid-Antibiotics, Satoschi Omura, Editor, Academic Press (1984), Part II, Chapter 9 which is incorporated herein by reference.

The present invention is based on the finding that Nys and Amp, being typical representatives of the polyene macrolides useful according to the invention, exhibit surprising therapeutical in vivo effects in a number of diseases when administered orally, intranasally or topically, which effects so far have not been described in the art and which cannot be theoretically explained by the above-mentioned conventional concept of the antimycotic mode of action.

The in vivo indications which have been surprisingly detected according to the invention comprise the following groups of diseases:

a) wounds and diseases with impaired wound healing,
b) diseases which are caused by immunoinsufficiency or associated with a temporary or chronic immunoinsufficiency,
c) cancerous diseases,
d) viral diseases,
e) diseases which are caused by an impaired cholesterol metabolism,
f) dermatological diseases caused by an impaired cell metabolism or cell transformation.

When trying to find an explanation for these surprising, novel therapeutical effects of the polyene macrolides, which were originally observed for Nys and Amp, the inventor was able to formulate a universal law for the biological regulation, the so-called "Bioenergenic Principle" (BP). This energy law describes the energy conversion in the cells and in the organism, and for the first time ever explains the biological regulation completely and from the standpoint of kinetics. The application of this law allows to logically and coherently explain all biological and medical phenomena known so far, including the novel modes of actions of polyene macrolides. The model substances for deducing the law were Nys and Amp. A "general theory of the biological regulation and medicine" was developed. This theory for the first time allows to uniformly explain the development of diseases in light of the most recent scientific findings. With the help of this theory the range of application of the polyene macrolides can be extended by a number of diseases and, as is obvious from the experimental part of the present description, can be confirmed in experiments.

The present invention is based to a large extent on the incidental and surprising finding that polyene macrolides, such as Nys and Amp, are resorbed by the gastrointestinal tract to a large extent and bring about systemic therapeutical effects which have not been observed so far.

As can be inferred from the BP, the effect of Nys and Amp is caused by a stimulation of the cell metabolism by cell depolarization and promotion of the energy conversion in the cells. This effect, which can be observed in all human cells, is of energetic nature and can be documented both by physical and mathematical data.

The invention is also based on the surprising finding that the chronic administration of high oral doses of polyene macrolides (about 10 to 50-fold higher doses than the short-time i.v. doses of comparable polyenes, such as Amp, which are generally administered every two days in an amount of 0.5 to 1.5 mg/kg body weight), results in various incurable chronic and systemic diseases being cured, without causing any side effects. It was furthermore found that their topical application in about 2 to 10-fold higher concentrations (about 200,000 to 1 million I.U./g basic ointment) than those usually recommended considerably accelerates the healing process of topical diseases, such as wounds, burns and trophic disorders, and brings on healing of various skin diseases.

These therapeutical in vivo effects are caused by the strong cell-stimulating and above all immunostimulating effect of polyene macrolides. The novel therapeutical effects can be explained by the characteristic molecular structure of the polyene macrolides drawing on the BP.

The present invention thus is based on a new understanding of paththogenesis which follows from the BP.

A particular subject underlying the invention is the use of polyene macrolides for the preparation of pharmaceutical compositions to be orally, topically or intranasally administered for the treatment of the diseases indicated in the claims and in the following part of the description.

The invention furthermore relates to therapeutical methods for treating mammalians, such as humans, suffering from at least one of the diseases indicated hereinbelow.

Further subject matters of the invention are evident from the experimental part of the description as well as from the attached claims.

DETAILED DESCRIPTION OF THE INVENTION

I. Introduction

In 1993 it was incidentally found that Nys and Amp, which so far have been only used as antimycotics against fungal infections, have various unusual therapeutical in vivo effects in the treatment of many diseases. Since then, many patients have been successfully treated. These novel therapeutical effects have not yet been described in the art. Up to the date of the making of the invention, there have been no clinical results for these indications. Starting from the present invention, it was possible to formulate a universal law for the biological regulation, which is referred to as "Bioenergenic Principle" (BP) and is an energy law. This law served to logically and coherently explain the regulation of the cell and of the organism, pathogenesis and the mode of action of drugs, including that of the polyene macrolides (=general theory of biological regulation). All biological processes, including our consciousness, are controlled energetically. The BP starts from the law of the conservation of energy and describes the energy conversion in nature. Employing the BP it was possible to develop an integrated model of the physical and organical matter. A detailed description of this theory is about to be published in the form of a book with HAUG Verlag, Heidelberg, Germany. A publication dealing with the topic was accepted by the journal "Medical Hypothesis", London, Great Britain.

So far, no theory has been available explaining the biological processes from an energetic and kinematic point of view. Also, there has been no general theory on pathogenesis and the pharmacological effects. It can be shown that numerous indications of known drugs are based on contradictory, hypothetical models. The BP gives reasons why these models are inapplicable and why most of the alleged therapeutical effects do not materialize in vivo.

The BP comprises 12 postulates; the postulates essential for understanding the present invention are summarized in the following section. These postulates will be referred to, to explain the cell regulation and the pathogenesis of important diseases which are treated according to the invention. They will be discussed in more detail in the general part.

Postulates of the Bioenergenic Principle

1. Matter/energy is self-organizing. There are innumerable levels of self-organization.
2. All levels of self-organization of matter are open systems. They exchange energy among themselves.
3. All levels of self-organization are disequilibrium systems. Every level of self-organization has an energy gradient which determines the system's disequilibrium. This energy gradient is referred to as "long-range correlation" within the Bioenergenic Principle.
4. The long-range correlation is the aggregated product of the energy contributions of all elements on a level (of a system).
5. The behavior of a disequilibrium system is globally determined by its long-range correlation (energy gradient). The behavior of all elements (degree of freedom) is determined by the long-range correlation in a uniform manner. A global behavior is always non-linear. Non-linear behavior is not predictable.
6. The long-range correlation of a system is maintained by continuous fluctuations (variations), which are the result of energy conversions within the system.
7. The extent of fluctuations of the long-range correlation determines the inner state of order (the inner entropy) of the system.
8. The propensity of a level of self-organization of maintaining its long-range correlation by fluctuations guarantees its stability. Stability requires an undisturbed energy exchange with other neighboring levels. An excessive disturbance of the energy exchange, which overburdens the compensatory mechanisms of the self-organizing level, inevitably leads to the partial or complete breakdown of the long-range correlation. Such a breakdown is referred to as "singularity" or "catastrophe".
9. The development towards a higher complexity is an inherent condition of all disequilibrium systems. The structural complexity ($K_E$) of a level of self-organization increases by time squared:

$$K_E = E.t^2$$

E is the energy exchanged during the time t. This law is called "the square time law of structural complexity" of "the law of evolution".
10. Every level of self-organization consists of many other levels and at the same time is part of other levels.
11. The energy conversion for any level of self-organization can be illustrated by the universal formula $$E_A = p.\lambda$$

for one conversion and $$E = E_A.f$$

for more than one conversions per time unit (p=impulse, $\lambda$=wave length of a fluctuation, f=frequency of the fluctuations, $E_A$=energy turnover of a conversion).

III. Cell Regulation Follows the BP

The cell and the organism are energetic entities. Without the supply of energy in form of food (substrates) there is no life. In the biosciences, the substrates are considered the carriers of chemical energy. All attempts to explain the biological regulation are made in the (bio)chemical field. Typically, physics does not consider the chemical energy an independent force (in physics, energy (E) and force (F) are often equated, although they are different physical variables, E=F.s, s=displacement). The four fundamental forces (also interactions) are: gravitation, the electromagnetic forces, the hadronic (strong) forces and the weak forces. The chemical forces in reality are electromagnetic forces. The ionic and the covalent bonds, the hydrogen bonds, the polar bonds and the van der Waals forces, which are responsible for chemical bonds, are only different forms of the electromagnetic forces. The two fundamental terms of chemistry—the molecular orbital and the covalent bond—are spatial abstractions and correspond to solutions of the wave function in quantum mechanics. From the conceptual and semantic standpoint, the (bio)chemistry is a metaphysical branch of physics. This is the first important pointer why so far it has not been possible to develop a coherent theory of the biological regulation.

In the following section, the essential steps of the cell metabolism are summarized in a consiced form and explained. Active intake of the substrates of food, the carbon hydrates (CH), the proteins and the fats, into the cell is either achieved by coupling to ion transports or by endocytosis. The important metabolic pathways in the cytoplasm are a complex redox cascade which produces intermediates. Together with the degradation products of the β-oxidation, these intermediates are combined with the mitochondria in the citric acid cycle and are further degraded. The cell metabolism is concluded in the respiratory chain (oxidative phosphorylation). Electrons and protons are the end product of the respiratory chain according to the stoichiometric formula $$O_2 + 4\ e^- + 4\ H^+ \leftrightarrow 2\ H_2O$$

The protons are pumped to the cytoplasmatic side of the mitochondrial inner membrane by a proton pump of the respiratory chain and form an electric (electromagnetic) gradient of about 220 mV. This gradient is coupled in a delocalized manner (chemiosmotic theory by P. Mitchell) to the production of ATP in the mitochondria. The ATP production is proportional to the mitochondrial gradient. ATP is provided to the cell metabolism. At present, ATP is considered the universal carrier of energy in the cell. Many reactions of the cell metabolism are ATP-coupled. The main share of ATP (50 to 70%) is consumed by the ATPases, for pumping ions ($Na^+$, $K^+$; $Ca^{2+}$) across the biological membranes against their gradient and to thereby build up electric potentials along the plasma membrane and other intracellular membranes.

This short explanation of the cell metabolism reveals a fundamental fact. As the end product of the entire cell metabolism electric membrane potentials are built up in the cell. All biological membranes possess electric gradients. The energy of the substrates is referred to as chemical energy although in reality it is the electromagnetic structural energy of the molecules. In this case it is obvious that the cell metabolism consists of countless conversions of chemical into electrical energy and vice versa: chemical energy of the substrates ↔ proton gradient of the mitochondrial membrane ↔ ATP production ↔ plasma membrane gradient, etc. From an energetical and balance point of view this fact has not been understood in bioscience. When taking due account of the law of the conservation of energy, one automatically arrives at the conclusion that the entire effective nutrient energy is converted to electrical energy of the membrane potentials of the cells. The effective nutrient energy is the energy which remains in the body after the deduction of heat being conveyed to the ambiance (about 60%), and which is effectively utilized for the body functions. If such a concept of the energy conversion of the cell were true, this would substantially influence the biosciences (see below).

This conclusion is made clear by an energy balance calculation for the human organism. For this balance, only known experimental data are used.

The average metabolic rate at rest of a human is about 1,500 kcal (=6,270 kJ). About 60% (3,762 kJ) is conveyed to the ambiance in the form of heat. The remaining effective chemical energy (structural energy) in the body is:

$$E_{eff} \cong 2{,}500 \text{ kJ } (25 \times 10^5 \text{ J})$$

In the following, it will be shown that the stored electrical energy ($E_{el}$) along the membrane potentials of the body cells can be equated with the $E_{eff}$. First, the number of all body cells must be calculated. If the average cell is considered a spheroid having a diameter of about 10 μm, an average cell volume of about $3 \times 10^{-16}$ m³ and an average weight of about $3 \times 10^{-13}$ kg, the number of all body cells (N) for an average body weight of 70 kg is:

$$N = 70 \text{ kg: } 3 \times 10^{-13} \text{ kg} = 2.3 \times 10^{14}.$$

The number of cells of our body is thus in the order of about $10^{14}$. This estimate corresponds with the numbers indicated in the literature.

In order to calculate the stored electrical energy of the membrane potential, the biological membranes are considered capacitors and the respective formulae of electrics are used. The outer side of the plasma membrane is considered the positively charged plate of a capacitor and the inner side the negatively charged side of the capacitor. The membrane resting potential of a body cell $V_R$ is −90 mV on average (such as in a heart muscle cell). The decisive value for the calculation, however, is the action potential $V_P$ which, due to the overshoot at the end of the depolarization phase, reaches a maximum potential difference of about 120 mV. During an action potential, the potential is discharged (depolarization) and the potential is built up again (repolarization). Therefore, in the balance calculation, the action potential $V_P$ of 120 mV is inserted as potential difference. The stored energy at the capacitors can be calculated with the formula $$E = \frac{1}{2} QV \quad (1)$$

(V=plasma potential and Q=charge). The charge $Q_P$ which is separated by the plasma membrane, is calculated from the formula $$Q_P = \frac{A_P \cdot V_P}{4 \cdot \pi \cdot k \cdot d} = \quad (2)$$

-continued $$\frac{3{,}14 \cdot 10^{-10} m^2 \cdot 120 \cdot 10^{-3} V}{4.3{,}14 \cdot 9 \cdot 10^9 N \cdot m^2 \cdot c^{-2} \cdot 20 \cdot 10^{-10} m} = 1{,}66 \cdot 10^{-13} C$$

($A_P$=surface of the plasma membrane, k is the Coulomb constant=$9.0 \times 10^9$ Nm²C⁻², d is the thickness of the lipid bilayer=$20 \times 10^{-10}$ m and $V_P$ is the voltage of an action potential=120 mV. The surface of the plasma membrane is $A_P = 4.\pi.r^2 = 3.14 \times 10^{-10}$ m² ).

From the membrane resting potential $V_R$=90 mV (absolute value) the maximum electric field strength $F_p$ can be calculated which a cell builds up in the plasma membrane:

$$F_p = \frac{V_R}{d} = \frac{90 \cdot 10^{-3} V}{20 \cdot 10^{-10} m} = 4{,}5 \cdot 10^7 V m^{-1}$$

The electric field strength of the plasma membrane potential thus is in the order of 10 million volt/meter. Such potentials are only built up when there is lightning in the stratosphere. Even if $F_P$ is effective in the shortest distances, all integral proteins and all cell elements are subject to this force to its full extent (see below). The electric field strength is a vector. It changes its size and direction during the course of an action potential and can temporarily acquire the value=0. According to formula (1) the electrical energy of the plasma gradient $E_P$, which is converted during an action potential, is $$E_P = \frac{1}{2} Q_P V_P = \frac{1}{2} \cdot 1 \cdot 66 \cdot 10^{-13} C \cdot 120 \cdot 10^{-13} V = 99{,}6 \cdot 10^{-16} J$$

$$E_P = 10^{-14} J$$

The electric potential of the mitochondrial inner membrane $V_m$ can also be experimentally determined and amounts to about 220 mV. Just like for the plasma potential in the cell, all relevant values for the mitochondria can be derived, too, and the stored electrical energy of the mitochondrial potential can be calculated: surface of the mitochondrial inner membrane (considering the cristae) $A_m = 4 \times 10^{-12}$ m², charge $Q_m = 0.39 \times 10^{-14}$ C, $F_m = 11 \times 10^7$ Vm⁻¹ and stored electrical energy of a mitochondrion is $E_M = 0.4 \times 10^{-15}$ J.

The energy of the plasma and mitochondrial potential accounts for the major part of the electrical energy of the cell. This is evident from the fact that the redox energy of the entire cell metabolism goes into the oxidative phosphorylation in the mitochondria and builds up the mitochondrial gradient and also because the major part of the cellular ATP production is consumed by the ATPases (e.g., Na⁺/K⁺-ATPase) of the plasma membrane. They pump ions against the gradient and build up the membrane resting potential (repolarization) after a depolarization (=release of the stored electrical energy). Since all intracellular compartments have electrical gradients—they often are measured as pH gradient (e.g., in the lysosomes)—they also store small amounts of electrical energy. Presently, this energy amount can only be approximately estimated. The entire electrical energy of a cell $E_{cell}$ can be calculated by adding the energy of the plasma potential and the energies of all intracellular potentials:

$$E_{cell} = E_P + n.E_m + E_{Golgi} + \quad (3)$$

$$E_{cell} = 1.10^{-14} J + n.0, 4.10^{-15} J + \ldots + \approx 10^{-13} J$$

(n is the number of mitochondria in the cell). In cells having a high energy turnover n is large. Muscle cells have densely packed mitochondria. Cells at rest contain only few mitochondria. A sustained repolarization of the cells causes the cristae of the mitochondrial inner membrane to flatten. The surface $A_m$ is reduced and thus also the mitochondrial electrical energy $E_m$ ($E_m$ is proportional to $A_m$). A sustained depolarization causes the cristae to enlarge. It is already evident from these examples that the cells are controlled via the electrical energy of the membrane potentials. The plasma potential and all intracellular potentials can be considered capacitors connected in series. Their potentials and energies can be added. They are in contact via the cytoplasm. The cytoplasm is governed by the law of electroneutrality. According to this law, the ion distribution is identical in any place of the cytoplasm. The plasma potential and the intracellular potentials are hence in a state of dynamic balance. Any depolarization of the plasma potential leads to an equivalent repolarization of the intracellular membrane potentials. Any intracellular repolarization leads to a corresponding conversion to chemical energy. An increase in the potential $V_m$ leads, e.g., to an increase in ATP production via the delocalized coupling.

During an action potential, which consists of a depolarization and a repolarization phase, the stored electrical energy of the cell is converted to chemical energy (depolarization) and vice versa (repolarization). Therefore, $E_{cell}$ can be equated with $E_A$. $E_A$ is the electrical energy which is released during an action potential and is converted to chemical energy in the cell.

$$E_{cell} \cong E_\lambda \approx 1.10^{-13} J$$

It is understood that the cell is no perpetuum mobile. More than 60% of the nutrient energy is conveyed to the ambiance in the form of heat. The cell requires constant energy supply in the form of substrates in order to maintain the energy conversions in its interior. In order to adapt the energy supply to the cell's requirements, it would have to be coupled somehow to the frequency of energy conversions (energy turnover). The cell in fact meets this requirement. The substrate supply in the cell is directly coupled to the energy conversion of the membrane potentials. The carbohydrate and amino acid transport across the cell membrane is energetically coupled to the $Na^+$ influx into the cell (symport). The $Na^+$ influx into the cell is responsible for the depolarization of the action potential. Thus, the coupling between energy conversion in the cell and energy supply from the outside is unequivocally explained. (in the last few years substrate symports which are coupled to other ion currents have been discovered). With every action potential, representing the specific, constant energy turnover of an individual cell, a certain (constant) amount of substrates is imported into the cell so as to meet the energy requirement of the cell metabolism. The action potential is an energetic "output" of the cell, the symport an "input" (see below). Due to its periodical action potentials or potential fluctuations the cell is continuously exchanging energy with the ambiance. The energy which a cell consumes per unit of time can be calculated by multiplying the energy turned over during an action potential, $E_A$, with the number of action potentials:

$$E = E_A \cdot f \quad (4)$$

(f is the frequency of the action potentials per time unit t). The energy which a cell, e.g., a heart muscle cell, turns over within the time t, depends on f as well as on the energy supply. Under stress, only the frequency f increases and the length of the action potential $\lambda$ decreases accordingly, while the size of the action potential $V_P$ and thus the energy $E_A$, which is turned over during an action potential, remains substantially constant. $E_A$ is then turned over in a shorter time. $E_A$ is a specific and over time fairly constant value for all cells. It depends on the intrinsic properties of the cell—the cell metabolism, the composition of integral proteins on the plasma membrane and other cell systems. The energy consumed by a heart muscle cell during one day can be easily calculated from formula (4). At an average heart rate of 72 beats/min a heart muscle cell experiences 103,680 action potentials (72 beats×60 min×24 h) in one day. This value will give an idea of the dynamics of the energy conversions in the cell. The concept of the cell as applied so far starts from a rather static understanding of the cell.

With respect to the energy turnover the body cells can be divided into three major groups: the group of the muscle cells (non-striated and striated), the group of the neurons and the heterogeneous group of the remaining cells. The cells of the first two groups are considered excitatory since they exhibit pronounced action potentials. Meanwhile, however, it is known that all other cells undergo depolarizations or repolarizations during their activity, even if these potential fluctuations are mostly less pronounced. Some cells of the $3^{rd}$ group can be referred to as resting cells, such as the resting cells of the immune system, others such as the tubular cells of the kidneys work under maximum stress. All physiological substances (hormones, neurotransmitters, lymphokines and other humoral immune factors) examined so far lead to potential fluctuations in the cells of this group. The de- or repolarization properties of the neurotransmitter, the lymphokines and the hormones in excitatory cells have been known for long.

The heart muscle cell can be considered a body cell with an average energy turnover. The striated muscle cells of the locomotor apparatus and the neurons have a considerably higher excitation frequency than the heart muscle cells. It varies between 5 (in striated muscle cells) and 100 (in some neurons) action potentials per second. These cells according to formula (4) have a higher energy turnover than the heart muscle cell. Measurements of the oxygen consumption in these tissues confirm this calculation. The cells of the third group on average have a lower energy turnover than the heart muscle cells.

Starting from these deliberations, the action potential of a heart muscle cell was considered earlier. $E_A$ of the heart muscle cell thus is $1 \times 10^{13}$ J. $E_A$ is the average electrical energy stored in the body cells and converted to chemical energy of the cell metabolism (structural energy) during an action potential. If $E_A$ is multiplied with the number of all body cells N, the aggregated product of the body's electrical energy is calculated which is turned over in our body in less than a second. Since the action potentials of the body cells in reality do not proceed synchronously, this energy can be compared with the stored electrical energy which is available in our body at any given time.

$$E_{A_N} = E_A \cdot N = 1.10^{-13} J \cdot 2,3.10^{14} = 23 J$$

This energy value, which results from a static(al) consideration of the metabolism, is very low. This circumstance could explain why so far the significance of electrical energy in biology has been neglected. If one calculates the dynamics of the energy conversions in the cells within one day, by multiplying with the frequency f, one arrives at a considerably higher energy value:

$E_{Ef} = E_{AN} \cdot f = 23J \cdot 103680 = 2385 kJ = 23.85 \cdot 10^5 J$ $E_{Eff} = 2500 kJ \approx E_{Ef} = 2385 \ kJ$ At the end of our energy balance calculation we arrive at the expected result: the effective chemical energy of the food which remains in our body is almost completely converted to electrical energy of the membrane potentials in the cells. This is a remarkable finding since a) for the first time an energy balance of our body on the level of the body cells has been established; b) the energy balance is based on experimental data of the electrophysiological science which have been known for many years; c) this balance was established using generally known physical laws (the law of the conservation of energy and the laws of electrics); d) despite some inevitable approximative values which result from the incredible complexity of the human body, we have succeeded in carrying out an exact balance calculation.

In this balance, the cells were considered immortal. In reality, however, the organism is in a continuous state of transformation. It is assumed that about 10 billion cells die per second. Some tissues, such as mucosa, are completely regenerated within a few days, others, such as neurons, persist. Taking into account a turnover rate of the cell transformation of about 3 to 5% per day, one arrives at an $E_{eff} = E_{el} = 2,500$ kJ.

In this balance calculation, the energy of those chemical substances that are discharged from the cell and participate in the supracellular regulation, is not calculated. The reason is that in the input-output model, on which the balance calculation is implicitly based, the energy of the substances discharged from all sells is equal to the energy of the substances which interact with them. Input and output therefore offset each other.

IV. Explanation of the Bioenergetic Principle Cell Regulation as an Example

It has been shown that the metabolism of organic matter can be sufficiently described with the general physical formula $E = E_A \cdot f$ (4). This formula applies both to the individual cell and to the entire organism. This is the starting point for the formulation of a universal law of energy conversion. The above-mentioned postulates of the BP represent the fundamental findings underlying the law in concised, descriptive form. These postulates of the BP shall be briefly explained by the example of cell regulation.

$1^{st}$ postulate: Starting from Einstein's law of the equivalence of matter and energy, matter must be considered bound energy. The $1^{st}$ postulate says that matter/energy is self-organizing. There are innumerable examples of self-organization in nature. The arrangement of lipid molecules in bilayers in ionic solution due to the different electromagnetical forces of attraction of the molecules is a classical example of the law of self-organization. It is no coincidence that biological membranes are the location of energy storage in the cell.

Both organic and inorganic matter consists of many levels of self-organization. A level consists of innumerable systems that are representatives of this level. The cell is the fundamental level of living matter. There are innumerable types of cells. It forms organs, organisms, species, evolution and consciousness as the most complex level of self-organization. On the other hand the cell consists of chemical molecules, elements and elementary particles (microcosm). All these parts together form the universe (macrocosm) which contains organic matter. All levels form a closed circuit. This self-contained nature of the universe is mainly clear from the law of the conservation of energy which forms the basis of the BP. An open universe would mean energy dissipation and contradict the law of the conservation of energy. The existence of self-organizing levels does not yet say anything about the mechanism of self-organization. The BP shows that it is an energetic process. The following postulates will explain this process.

$2^{nd}$ postulate: Within the universe all levels or their systems are open, i.e., they exchange energy among themselves. They can be illustrated by a complex input-output model. The cell and the organism, e.g., are open systems and exchange energy (heat, food, work) with the ambiance. A disruption of the energy exchange leads to death=dissipation of the self-organization of these levels.

$3^{rd}$ postulate: All levels are disequilibrium systems and every level has its energy gradient which determines the system's degree of disequilibrium. According to this definition, the disequilibrium is an energy gradient. When the energy gradient reaches the value 0, the system is in balance. The balance is not the normal state every system tries to achieve but only a special case. The normal state is the disequilibrium. In the cell the electrical membrane gradients determine the disequilibrium. The electric field strength of these gradients is in the order of 10 million volt membrane resting potential. It can temporarily acquire the value 0 during an action potential.

The energy gradient of a level or its force is the motor driving self-organization. We call this force the long-range correlation, LRC.

$4^{th}$ postulate: The LRC is the aggregated product of the energy amounts of all elements of a disequilibrium system. This was proven by the balance calculation. The energy which is released from the entire cellular metabolism is converted to the electrical energy of the membrane gradients and vice versa. The $4^{th}$ postulate can also be defined like this: the LRC is the energy integral of all energy inputs of the system at a certain time. LRC is a dynamic value and changes constantly within an action potential. The fluctuations of the LRC are of periodical nature. The energy value of an action potential remains fairly constant over time.

$5^{th}$ postulate: The LRC determines the behavior of the disequilibrium system; therefore the designation long-range correlation. In the cell an electric field strength $F_E$ is exerted which is in the order of $10^7$ $Vm^{-1}$ (SI units). The chemical balance of all reactions in the cells is displaced by the same order. We will illustrate this fact for the ATP cleavage. The balance of the reaction ATP $\leftrightarrow$ ADP+P*, which is conventionally considered the universal source of energy of the cell, is on the right side: ATP (Mol): ADP (Mol)=$10^{-6}$ (Mol is the SI unit). In the cell, however, there is a different ratio (Atkinson's ratio) ATP:ADP=10:1. Thus, the balance is displaced by the factor $10^7$ to the left, in favor of ATP. Many reactions in the cell are coupled to this reaction and they are in the same state of disequilibrium. The primary cause, however, is not the disequilibrium of the ATP reaction but the electric field strength which determines the disequilibrium of all reactions in a uniform manner.

In a system the behavior (degree of freedom) of all elements is determined by the LRC in a uniform manner and simultaneously. To the extent in which the LRC becomes smaller, the degree of freedom of all elements increases. The term "degree of freedom" describes the local energies of the system's elements which increase once the LRC decreases (=law of the conservation of energy). The increase in the degree of freedom leads to energy conversions which rebuild the LRC (periodicity). The degree of freedom of the biochemical structures in the cell is to enter chemical reactions which rebuild the $F_E$ of the membrane gradient. ATP is degraded to ADP and P* in order to pump ions against the gradient and to restore the membrane resting potential. Every reaction in the cells proceeds specifically. The reaction rate of all reactions, however, is determined globally and in a uniform manner by the electric field strength. In an action potential $F_E$ acquires different (infinitely many) values. This accounts for the finely tuned adaptation of the cell metabolism. The LRC (=the $F_E$ of the membrane gradients) is the driving force of cell regulation.

The LRC globally determines the degree of freedom of all elements of a system. The global behavior of all disequilibrium systems has been sufficiently explained by the chaos theory. The LRC and the energy amounts of the system's elements form a recursive, retroactive system via the energy conversion. In this manner the initial conditions of the disequilibrium system continuously change. The behavior of such systems is known to be nonlinear and therefore not predictable. This postulate integrates the most important findings of the chaos theory.

Reflexes, adaptation of the organisms to the environment, diseases, etc., are always global events. Despite this, the fundamental paradigms in the biosciences (key-lock concept, messenger concept, receptor specificity, specific effect of drugs, etc.) start from a specific, local behavior of organic systems (reductive-deterministic view). The BP leads to a fundamental change of the paradigms in science (Kuhn, Lakatos). All results have global character and can only be understood in their globality. They also overthrow the principle of causality (see Hume) which is presently predominant in medicine. The BP allows for a logical and coherent theory on the etiology of all diseases under prospective consideration of the most recent experimental results in this field (see below).

$6^{th}$ postulate: The LRC is maintained by continuous fluctuations (or action potentials) which are the product of energy conversions in the system. The energy exchange with the neighboring levels proceeds via these fluctuations. We have shown this fact for the substrates. The carbohydrate and protein symport into the cell is coupled to the depolarization of the plasma potential (Na-influx). An action potential is an inherent property of the system. It is the energy product of the entire system and is therefore system-specific. The amount of energy $E_A$ is fairly constant. The energy turnover can only be increased or reduced via the frequency f, i.e. $E=E_A.f$. Continuous fluctuations are the prerequisite for the maintenance of the LRC and thus for the maintenance of the disequilibrium in the system. "Disequilibrium is life—equilibrium is death" (E. Schroedinger, Was ist Leben, 1943). An undisturbed energy exchange with the neighboring levels is therefore imperative for the maintenance of the LRC (see next postulate).

$7^{th}$ postulate: The inner state of order (entropy) depends on the periodic fluctuations of the LRC. This postulate is derived from the $5^{th}$ and $6^{th}$ postulates: the entropy (S) of the system results from the degree of freedom (Z) of all elements of the system ($dS=R.lnZ_1:Z_2$, dS=change of entropy, R=universal gas constant, $Z_{1,2}$=degree of freedom). The proper course of an action potential is decisive for the function of the system's elements. The adequate contraction of a muscle cell predominantly depends on its action potential. The action potential represents the conversion of an amount of energy $E_A$, which is fairly constant for any system. $E_A$ is a function of the system and predominantly depends on the undisturbed exchange of energy with the neighboring levels ($6^{th}$ postulate). It can be shown that all physiological factors have pronounced dipole properties and promote the energy conversion of the membrane potentials. The peripheral neurotransmitter, acetylcholin, e.g., leads to depolarization, the central inhibitory neurotransmitter, GABA, to repolarization. The molecules of the two substances are pronounced dipoles.

If energy conversion is inhibited—any inhibition is also of energetic nature—the cell's output is reduced. Chemical substances having certain dielectric properties inhibit energy conversion at the plasma membrane. 90% of all drugs which are currently on the market, possess such properties. They are defined as cell-inhibiting. Their actual designations refer to their cell-inhibiting properties (β-blocker, Ca antagonists, antiarrhythmics, cytostatics, immunosuppressants, etc.). These drugs prolong the action potential, i.e., the wave length (λ), and thus reduce the frequency (f). However, the energy turned over by a cell is proportional to the frequency, $E=E_A.f$, since $E_A$ is constant; i.e., these drugs reduce the energy turnover and thus the energy production of the cells. They inhibit the energy conversion in the cells. The result is: manifold side-effects, reduced functionality (e.g., reduced immune response), increased mortality and cancer. Various large-scale, sophisticated, placebo-controlled double-blind studies in the last few years substantiate the conclusion which must inevitably be drawn from the BP (CAST study; Concorde study; Cyclosporin bei Transpantationspatienten, Lancet, Vol. 342, 1993, 1514–16; etc.). On the other hand, there is not a single large-scale placebo-controlled study which substantiates a clear advantage of a chronic therapy with cell-inhibiting drugs measured by the primary (endpoints) test parameters mortality and healing.

The impaired efficiency of the cells brought about by a medical inhibition of the energy transmission and the corresponding toxicity and mortality is easily comprehensible, the increased cancer risk, however, not. And yet, the increased cancer risk observed when the cells are inhibited originates from a uniform energetic cause as the increased mortality and toxicity. An inhibition of the physiological periodicity of the action potentials results in an increase in the inner entropy, the degrees of freedom of the elements in the system. When the inner entropy increases, the system's propensity of changing augments, too. This results in various phenomena in the cell. It is possible, e.g., to change the entropy of the cells/bacteria by subjecting them for a short period to great thermal fluctuations and to thereby increase the mutation rate. The same phenomenon can be observed when cell-inhibiting drugs are administered chronically. The increased cancer risk (250 drugs of the WHO list with proven carcinogenicity have dielectric properties which identify them as cell-inhibiting agents) can also be explained from the energetical point of view. A potential fluctuation, an action potential, can be considered an envelope (wave) which is composed of many smaller waves (Fourier analysis). From the physical point of view the many smaller fluctuations which form the action potential are electromagnetic waves which expand in the cell. Electromagnetic waves always expand. The cytoplasm as ionic solution is an optimum medium for their expansion. The expansion of electromagnetic waves in the cell has been theoretically worked out a some time ago (Fröhlich, H., Coherent Excitation in Active Biological Systems, in Modern Bioelectrochemistry, 1986, Plenum Press, New York, 241–262). The existence of coherent electromagnetic waves in the cells is a fact and is made use of by the SQUID method (Superconducting Quantum Interference Device) in biomagnetic brain research. The waves form interference patterns, e.g., in the cell nucleus (the nuclear pores having a diameter of from 50 to 100 Angstrom function like grids)

and cause local energy maxima. When $F_E$ is becoming smaller during a depolarization, the local maxima at the biochemical structures increase—as does the rate of the chemical reactions (law of the conservation of energy).

The theoretical fundamentals how such maxima come about on the quantum level have already been developed. For example, solitons (standing waves) in the DNA (Muto v et al. Solitons in DNA, J. Biomol. Structure & Dynamics, Vol. 5, 1988, 873–94) and in other structures (Davydov AS, Excitons and solitons in molecular systems, Int. Rev. Cytology, Vol. 1987, 183–225, Bednar J. Electronic excitations in condensed biological matter, Int. J. Radiat. Bol., Vol. 48, 1985, 147–66) can occur by electron transfer within the supramolecular biostructures which control the bioprocesses kinematically or by configurational changes. The DNA comprises one or more peak solitons which are capable of moving along the DNA strands without dispersing and to thereby control the transcription process. First experimental results prove that the DNA strand is conductive for electrons and thus meets the energetic requirements for forming solitons (Murphy C. J. et al., Long-range photoinduced electron transfer through a DNA-helix, Science, Vol. 262, 1993, 1023–29). An inhibition of the energy conversion of the stored electrical energy of the membrane potentials by cell-inhibiting drugs impairs the formation of DNA solitons via the expansion of electromagnetic waves in a delocalized manner. The probability (the degrees of freedom/the entropy) increases that incorrect nucleotides are inserted during the transcription process. This is the energetic mechanism of all mutations. The cell requires a certain plasticity in order to change under unfavorable conditions. This mechanism is physiologically used by the stem cells in the bone marrow to produce specific lymphocytes (colony-stimulating factors). A mutation can be positive or negative in the energetical sense. The transformation of a cell into a cancer cell is triggered by mutations which occur more frequently under the constraint of unfavorable energetic conditions. Such mutations always have energetically advantageous effects for the cell (over-production of growth factors or the conversion of protooncogenes by point mutations to oncogenes). The BP allows remarkable insights in this context (see soliton triplets in item V).

$8^{th}$ postulate: Every level remains self-organizing as long as it is capable of maintaining its LRC, i.e., as long as it is undisturbed in the exchange of energy with the neighboring levels and produces fluctuations. A sustained cell inhibition inevitably results in cell lysis. A sustained over-depolarization or over-repolarization causes apoptosis (programmed cell death) because the energy conversion and thus the regular up and down of the LRC cannot take place. The cell regeneration in the organism and the entire immune regulation (e.g., the MHC-restricted T cell selection in the thymus) is based on apoptosis. It is a physiological process. The bioenergetic cause of apoptosis could be elucidated by formulating the BP.

V. Mode of Function of the Membrane Proteins within the Meaning of the BP

In the above discussion the entire cell was looked at from a bioenergetic standpoint and the membranes were interpreted as capacitors. In reality, the membranes are complex structures. They consist of various lipids and membrane proteins (integral proteins). About 50% of the membrane weight accounts for the membrane proteins. The BP furnishes a convincing explanation for their energetic function.

There are three major functional groups of membrane proteins: the receptors, the ion channels and the ion pumps (ATPases). Their orientation in the membrane is determined and is directly functionally connected with the polarity of the membrane potential: an ATPase, e.g., becomes an ATP synthase once the membrane potential changes its polarity. Most receptors have their $COO^-$ end in the cytoplasm and the $NH_3^+$ end in the extracellular space (e.g., the receptors of the seven loop type). The receptors never change their polarity (no flip-flop). The ion channels point with their two ends either into the cytoplasm ($Na^+$ channels) or into the intracellular space (GABA receptor—actually, it is a $Cl^-$ channel). The ion pumps are composed of several polypeptide chains and their $COO^-$ and $NH_3^+$ ends are located both in the cytoplasm and in the extracellular space. The specific orientation of the membrane proteins is functionally connected with the polarity of the membrane potentials. This is particularly evident from the fact that they bring about the ion transport (transport of charge) across the membrane either directly (channels and pumps) or indirectly (receptors). When the receptors are activated, discreet modulations of the plasma potential occur, which in turn open voltage-gated channels. In summary, the following can be stated: a) all biological membranes have numerous integral proteins; b) all membrane proteins change the membrane potentials by de- or repolarization and participate in this manner in the origination of an action potential. The membrane proteins are responsible for the conversion of the electrical energy of the membrane potentials into chemical energy in the cell. The cell regulation from outside thus proceeds via the membrane proteins, i.e., via the LRC. The other cytoplasmatic proteins of the cell, which have enzymatic and regulatory functions, are uniformly controlled via the LRC. They provide structural energy (ATP, new membrane proteins, etc.) which allows to build up the electrical energy of the plasma potentials.

Starting from BP it was found that certain protein structures play an important role for the charge transport both in membrane proteins as well as in the enzymes. There are two basic structures of proteins which substantially determine the tertiary and quaternary (three-dimensional) structure: the α-helix and the β-pleated sheet. All integral proteins consist of a transmembrane part and of loops which are located outside the membrane—cytoplasmatically or extracellularly. The transmembrane part of the integral proteins is uniformly structured as α-helix. A membrane protein usually comprises several α-helices. Every α-helix has its individual structure—one side of the coils (about 180°) is made up of lipophilic amino acids while the other side is made up of hydrophilic amino acids. The α-helices—following the law of self-organization—orient themselves with their lipophilic sides towards the phospholipids of the lipid bilayer and with the hydrophilic sides towards each other. In this manner, they form hydrophilic channels in the membrane. These channels in inactive condition are closed for ions.

The ion transports across the membrane, which effect the de- or repolarization of the cell and which in the final analysis are responsible of the conversion of electrical energy, run exclusively along the membrane proteins. All models contemplated so far, e.g., for ion channels or for $Na^+$-$K^+$-ATPase (e.g., the Jardetzky model) consider only the protein structures and fail to see the importance of plasma potential and of energy conversion for the cell regulation. Starting from the BP a new model is proposed which is both theoretically substantiable and experimentally verifiable. Nevertheless, it must be assumed that the processes on the quantum level are far more complex than the ones described by us. From an energetical and balance standpoint, however, this description is perfectly sufficient to adequately describe the regulation of the cell and the organism and thus to logically and coherently explain the experimental results of modern biosciences.

It was found that certain amino acids are essential for the transmission of charge along the supramolecular structures of the proteins. Among the 20 amino acids there are two positively charged amino acids (+amino acids)—Arg and Lys—, two negatively charged amino acids (−amino acids) —Asp and Glu—and three π-electron carrying amino acids (π-amino acids)—the essential, aromatic amino acids, Phe, Tyr and Trp. In α-helices, one +amino acid, −amino acid and π-amino acid each form a functional dipole. This functional unit is referred to as the "soliton triplet". An analysis of the amino acid sequences of many proteins, the structures of which have been elucidated in the last few years, shows that three amino acids each of a soliton triplet are in vicinity to each other. A π-amino acid is flanked by a −amino acid and a +amino acid. Such structures can be found mainly in α-helices, but also in β-pleated sheets. Soliton triplets are surrounded by lipophilic amino acids which form a lipophilic environment around these functional units so as to protect them against the ionic environment of the cytoplasm or the extracellular fluid. In enzymes and membrane proteins which consist of alternating α-helices and β-pleated sheets, such soliton triplets can be found in the functional centers, e.g., in Tyr-kinases, in the peptide-binding pockets of MHC class I and II proteins (L. J. Stern, Crystal structure of the human class II MHC protein HLAS-DR1 complexed with influenza virus peptide, Nature, 368, 1994, 215–221), in hemoglobin (L. Stryer, Biochemistry, W. H. Freeman & Company, 1988) etc. These hydrophobic (lipophilic) centers have contact with the outside via hydrophilic amino acids. Hence, all 20 amino acids which take part in the formation of proteins have functional importance. The AS sequences which can be observed in the proteins reflect the nucleotide sequences of the genes. They can be read in terms of their energetic or functional importance. Thus, the genetic code is not the a priori event which determines everything in the cell, as is presently believed, but a structural complexity which is the result of the evolutionary law ($9^{th}$ postulate) and is subject to the energetic force of the LRC. According to the BP, the organization or the conversion of energy in the cell is the primary event.

The soliton triplets are responsible for the transmission of the charge. A protein possesses several soliton triplets. They can be considered the molecular wires which function in the membrane potential as semiconductors. The +amino acids and the −amino acids function, depending on their polarity, as electron donors or electron acceptors. The π-amino acid is the electron-conducting structure between the two. Countless data of the supramolecular chemistry confirm the electrical properties of such biological molecular wires (e.g., M. Wassielewski, Photoinduced electron transfer in supramolecular systems for artificial photosynthesis, Chem. Rev., 1992, 92, 435–461). These properties can be detected also in biological structures—for example in rhodopsin (U. B. Kaupp et al., Primary structure and functional expression from complementary DNA of the rod photoreceptor cyclic GMP-gated channel, Nature 342, 1898, 762–66) but also in DNA (see above) and in other structure (myosin-actin filaments, cytoskeleton, etc.). Gene mutations and particularly point mutations which relate to the soliton-specific amino acids are always accompanied by a functional disturbance—the transmission of energy (charge) is impaired. Such acquired or hereditary mutations lead to diseases. The genesis of the disease can thus be explained on the energetic level.

The soliton triplets can be used to explain how the ion channels and the ATPases function. The electron donor of a soliton triplet which is located in the α-helix of a membrane protein can emit an electron due to a modification of potential. In the inactive state, the $E_P$ as LRC makes sure that the degree of freedom of the electrons remains limited. The emission of an electron can therefore only be brought about by fluctuations of the potential. This electron is temporarily taken up by the π-amino acid. Due to their energetic level the π-electrons can be found in the entire π-structure. Such a structure can easily take up additional electrons. The unpaired excess electron preferably assumes localized, energetically advantageous positions, the so-called "mid-gaps", in the π-system. Such "mid-gaps" display a negative charge—the charge of an electron. The "mid-gaps" may move along the π-electron structure. In this manner they are transferred to the electron acceptor. In this case, the "mid-gaps" are provided with a positive charge— the charge of a proton. The positive "mid-gaps" move in opposite direction. They can also be transferred to other structures (Karplus M & Porter RN, Atoms & molecules, 1970, Benjamin/Cumming Publishing House, 1970). The same phenomenon can be observed in solid-state semiconductors (see also quantum theory of electric transmission, Fermi-Dirac distribution function, etc.). In this manner, protons are transported across biological membranes (e.g., in the proton pumps of the respiratory chain). The transmission of a single electron along a membrane protein, e.g., along the transmembrane part, effects a global change of configuration of the entire protein structure. The result are standing waves, so-called solitons, which do not disperse but propagate along the structures. The formation of solitons (referred to also as excitons) in membrane proteins was first theoretically corroborated by Davydov (see above). The mathematical theory of the solitons had been formulated earlier by other physicists (Zakharov and Fadeev 1971, Zakharov and Shabat 1974, Cologero and Degasperis 1976, Bullough and Caudrey 1980, etc.) and dates back to the research of non-linear systems (first by Fermi, Pasta and Ulam in Los Alamos, 1955). It is important for the present discussion to state that the transfer of a single electron at one end of the membrane protein is sufficient to change its entire configuration. Such configurational changes can be very well observed, e.g., in rhodopsin after take-up of a photon by retinal (L. Stryer, Cyclic GMP Cascade of vision, Ann. Rev. Neurosci., 1986, 9, 87–119). Recently, global configurational changes were observed for fullerenes of the $C_{60}$ type and for other cage compounds in which a laser is used to excite a single electron to a higher energy level (presentation of the group M. Benati et al., Universität Stuttgart on the spring symposion of the Deutsche Physikalische Gesellschaft in March 1995 in Berlin).

Solitons temporarily change the structure of the ion channels and the ATPases and open in this manner the hydrophilic channel which they form in the membrane. The electron transfer which can be observed in the integral proteins, leads to ion fluxes along the ion gradient (ion channels) or against the ion gradient (ATPases) by configurational changes. In the inactive state the proteins and thus their soliton triplets are in a configurational condition in which an electron transmission via the π-electron structure is impossible—in this state a prohibited energy band or conduction band is formed which can only be neutralized by an activation, e.g., receptor activation, from the outside or by a change of the potential.

The receptors work according to the same laws, although they do not conduct ion fluxes across the membrane but only electrons. They bring about discreet potential fluctuations which can open the voltage-gated channels. Thus, all membrane proteins fulfill the function of a semiconductor. They conduct electric currents across the membrane in a specific direction and thereby influence the LRC of the cell. Their semiconductor properties depend on the magnitude and the direction of the membrane potential. This explains why they have to have a specific orientation and why an ATP-ase is converted to an ATP-synthase once the direction of the membrane potential is reversed. All membrane proteins and all other cell proteins are functional units which are based on the same mode of action—they only are variations of the same principle and are universally applicable. Reconstitution experiments show that membrane proteins which are derived from different species—for example a bovine ATP-ase and the bacteriorhodopsin of an archaebacterium which functions as proton pump—can be coupled to one another via the membrane potential and perfectly work although they have never met before (Racker, E. Reconstitutions of transporters, receptors and pathological states, Academic Press, 1985).

The activation of membrane proteins usually is accompanied by an endocytosis. Most receptors are taken up in the cell after activation and are either degraded or emerge again after a certain time at the cell surface. The cell is subject to different initial conditions at any point of time which substantially and always globally determine its behavior in response to external influences. Whether a cell is depolarized or repolarized and to what extent this is done, does not only depend on the aggregated product of all physiological factors of the supracellular regulation which interact with the cell but also on the initial condition of the cell. In the following, we will summarize some important results which can only be explained by the BP.

If the cells are increasingly depolarized, for example by a larger amount of depolarizing substances, their overall metabolism increases. They grow, produce more protein and increasingly divide. An increase in endocytosis of the membrane proteins is the result. Depolarizing substances have a cell-stimulating effect. They increase the energy turnover of the cell by mainly increasing the frequency of the potential fluctuations according to the universal equation of the BP, $E=E_A.f$. Repolarizing substances increase the threshold of cell activation and reduce the cells' energy turnover via a reduction of the $E_A$ frequency. An increased stimulation by repolarizing substances results in cell maturation, cell differentiation and increased expression of membrane proteins. Both forms of the cell regulation proceed simultaneously and are indispensable for the biological regulation. Whether a cell is mainly depolarized or repolarized, depends not least on its initial conditions—such as the composition of the plasma membrane proteins. In the physiological regulation the depolarizing factors predominate by far—there are about 20 depolarizing interferons but only one repolarizing interferon.

Most peripheral neurotransmitters which activate the muscles and provide the primary neuronal stimuli, have a depolarizing effect. Repolarizing neurotransmitters predominate the central nervous system and serve to modulate the primary conduction by repolarization at the synapses. First, a depolarization takes place and then a repolarization. Excess and sustained depolarization leads to apoptosis (programmed cell death, also called cell lysis) through a dissipation of the LRC. An excess and sustained repolarization leads to anergia of the cells (the energy turnover sharply decreases) and to cell death (=apoptosis). The energetic cause of apoptosis could only be explained once the BP was discovered. Apoptosis is a physiological process. Regeneration of the cells and of the organism which is essential for the body's health is brought about by apoptosis. Regulation of the immune system, the development of self-tolerance and alloreactivity is based on apoptosis. This finding is important for the understanding of the mode of action of Nys in many immunological diseases.

VI. The Mode of Action of Polyene Macrolides Corresponds to the Mode of Action of Membrane Proteins The mode of action of the polyene macrolides can only be fully understood if one knows the mode of action of the membrane proteins and takes the cell regulation according to the BP into consideration. Hence, all explanations so far attempted have failed to provide an understanding of the polyene macrolides in this respect and have failed to recognize its therapeutical potential. The mode of action of the polyene macrolides useful according to the invention is explained by the exemplary compound Nys in more detail in the following sections. The following explanations apply in analogy to Amp.

1. The Structure of Nystatin

Nys, like all polyenes, consists of two different chemical structures, namely a macrolide ring and an amino sugar. The amino sugar, a mycosamine (3-amino-3,6-dideoxy-D-mannose) is glycosidically attached to the macrolide ring. The macrolide ring consists of carbon atoms and is closed by the formation of an internal ester or a lactone. The macrolide ring is a stable rod-shaped structure with a hydrophobic side which is built by the polyene chain ($\pi$-electron carrying structure) and an opposite hydrophilic side which is built by the hydroxyl groups. The conjugated double-bonds of the polyene chain are in the trans-position. The sugar moiety is bonded at the one end of the macrolide ring and carries a primary amino group. At the same end, a carboxyl group is present on the macrolide ring. A single strongly polarized and hydrophilic hydroxyl group is positioned at the other end of the macrolide ring and imparts to this part of Nys hydrophilic properties. The amphiphilic character of Nys is determined by the entirety of these groups. They are responsible for the orientation of the molecules in biological membranes. There is strong evidence that the sugar moiety and the carboxyl group are on the extracellular side of the membrane while the strongly polarized hydroxyl group is on the cytoplasmatic side, although flip-flop phenomena cannot be completely precluded. The orientation of Nys in the membrane thus corresponds to that of an integral protein. All membrane proteins are glycoproteins and their glycosidic part is always on the extracellular side. This rigid orientation of the membrane proteins is connected with their specific function.

In the bioenergetic sense, the structure of Nys exhibits all functional groups that can also be found in the membrane proteins and that determine their mode of action as semiconductors or energy transporters. The long macrolide ring corresponds the transmembrane part of the integral protein. Like the $\alpha$-helix, it possesses a hydrophilic side and a lipophilic side which consists of a long $\pi$-electron chain. The amphipathic character of Nys determines its self-organization in the lipid bilayer. The macrolide ring protrudes into the membrane. It is about 22 to 25 Angstrom in length and is about as long as the $\alpha$-helix of a membrane protein. The sugar moiety determines its orientation. Nys has two charged groups, one positively charged (the $NH_3^+$ group at the sugar moiety) and the other negatively charged (the $COO^-$ group at the macrolide ring) which are in vicinity to the $\pi$-electron chain. They act as electron donor and electron acceptor, depending on the voltage polarity. Nys thus possesses a soliton triplet, just as the membrane proteins. It functions like a semiconductor in the membrane potential and allows the ion transport across the membrane. Nys is known as ionophoric. The dipole character of Nys is determined by the strongly polar hydroxyl group at the opposite end of the macrolide ring, the π-electrons of the polyene chain and the positively and negatively charged groups. When starting only from the charge of the π-electrons that can move freely in the polyene chain and can undergo a polarization under the membrane potential, one can estimate the dipole energy of Nys:

$$E_D = q.l.F_p \approx 10^{-19} J$$

(q=n.e, number of π-electrons, n=12 for Nys, n=14 for Amp; l=22×10$^{-10}$ m length of the π-electron chain, $F_P$=4.5×10$^7$ Vm$^{-1}$, electric field strength of the plasma potential, e=1.6× 10$^{-19}$ coulomb). The dipole energy of a Nys molecule is smaller by factor 10$^5$ than the energy of the plasma gradient E=10$^{-14}$ J. The energy turnover between the levels of self-organization proceeds in energy packages, energy quantums, with fixed energy amounts. A Nys molecule under the given conditions ($F_P$) has a specific energy value. The energy values of such packages have a statistical distribution around the most frequent energy value. The dipole energies of the most cell-stimulating substances are in the range of 10$^{-19}$ J. The energy of an electron in $V_P$ is 0.19×10$^{-19}$ J.

It is conventionally believed that Nys binds to cholesterol or ergosterol, with the affinity to the latter being stronger. At present, from this belief a "specific" antimycotic effect is derived. This is a classical example of a reductive-deterministic, and, i.e., mechanistic explanation. For one thing, any biological membrane consists of structural lipids, phospholipids. If the phospholipids are present in an ionic solution, they organize themselves immediately to a bilayer due to their amphipathic properties. The same holds true for cholesterol or related chemical substances such as the steroid hormones but also for the ergosterol of fungal membranes. This phenomenon can also be observed for all membrane proteins. As soon as they are in contact with the lipid bilayer, they organize themselves by forming α-helices and loops. All constituents of biological membranes organize themselves. Nys also organizes itself in the membrane. Due to its amphipathic properties it exhibits a pronounced affinity to biological membranes and binds spontaneously. All these forms of self-organization are energetically controlled. In biological membranes the cholesterol is present in a molar ratio of about 1:1 to the phospholipids. However, its concentration may vary widely—particularly in intracellular membranes. Due to the narrow spatial conditions in the membrane Nys necessarily has to enter into contact with cholesterol. But it just as well enters into contact with all other membrane lipids and protein structures. It is a fundamental error to explain the effect of Nys with a single interaction with a single element of the membrane (see de Kruiff's model in Polyene antibiotic-sterol interactions in membranes of Acholeplasma laidlawii cells and lecithin liposomes, Biochimica and Biophysica Acta 339, 1974, 57–70). Hence, the explanation given so far for the antimycotic effect of Nys is not correct. Due to its specific molecular structure Nys can be considered a universal non-proteinaceous ion channel. Such an interpretation explains its ubiquitous ionophoric properties (see item 2 below). In this capacity it predominantly influences the plasma potential of the cells and thereby enters a global energetic interaction with all membrane and cell constituents. Furthermore, direct bindings to cholesterol may occur.

The energetic interaction between Nys and cholesterol is paramount for its therapeutical effects, such as in arteriosclerosis. Cholesterol is essential for the energy conversion on biological membranes. Its function could be defined anew within the sense of the BP. According to the dipole model, the cholesterol molecule has almost no dipole character. Its dielectric properties distinguish it as strong biological insulator. Cholesterol therefore determines the insulating properties of the biological membranes and not only their fluid character. In view of the extremely high $F_E$ of 10$^7$Vm$^{-1}$ the biological membranes have to be strong insulators. On the basis of this concept the effect of all steroid hormones, such as the sex hormones and the glucocorticoids can be explained. They are built from cholesterol and have a stronger dipole character than cholesterol—the aliphatic moiety of cholesterol is replaced by polar groups. As soon as polar cholesterol derivatives are mixed in small amounts with cholesterol in the membrane their conductivity is slightly increased. In physiological concentrations the sex hormones therefore have a cell stimulating effect and promote cell growth—e.g., in the fetal development and during puberty. If, however, they are administered in considerably higher concentrations, such as during therapy with glycocorticoids, they excessively increase the conductivity of the biological membranes. The original level of the membrane potentials V and thus of the stored electrical energy E cannot be maintained due to the unfavorable dielectric properties of the membranes—V and $E_{el}$ are inversely proportional to the dielectric constant ε of the membrane. Consequently, the energy turnover of the cell is reduced. In higher concentrations all glucocorticoids therefore have cell-inhibiting and above all immune-inhibiting effects. This gives an energetical explanation of the etiology of arteriosclerosis/atheromathosis (see below).

2. Pharmacology and Kinetics of Nys within the Meaning of the BP

On the basis of the Nys structure all known pharmacological effects of this polyene macrolide and all others used according to the invention can be explained logically and coherently within the meaning of the BP. On top of that, all new therapeutical effects that are the subject matter of the present invention can be substantiated. First the known ones: Nys is, as already mentioned above, ionophoric. Therefore it is widely used in the patch-clamp technique. Nys is said to increase the membrane permeability to ions. In biological membranes an increased permeability to Na$^+$ and K$^+$ ions can be mainly observed. In cell cultures there is a Na$^+$ inflow and a K$^+$ outflow along the ion gradients. Nys leads to a depolarization in all cell types examined so far. Furthermore, it modifies the membrane permeability to other ions. Nys increases, e.g., the intracellular concentration of Ca$^{2+}$ (Wiegand et al, Nystatin stimulates prostaglandin E synthesis and formation of diacylgycerol in human monocytes, Agents and Action, vol. 24, 3/4, 1988). In this case this is a consequence of the global stimulation of the cells by Nys. Any cell stimulation is accompanied by an increase in intracellular concentration of calcium. Therefore, calcium is incorrectly referred to as "second messenger". All intracellular systems examined so far that are stimulated by way of a cell activation and can be considered indicators of such cell stimulation—and not as "second messengers"—are activated by Nys. Nys, just like Amp, stimulates the production of the prostaglandins, the phosphoinositol cascade (Wiegand et al.), the adenylatcyclase cascade (Dipple I & MD Housley, Amphotericin B has very different effect on the glucagon- and fluoride-stimulated adenylat-cyclase activities of rat live plasma membranes, FEBS Letters, 106, 1979, 21–24), DNA- and RNA synthesis and the substrate transport (Kitagawa, T. & Andoh, T. Stimulation by Amphotericin B or uridine transport, RNA synthesis and DNA synthesis in density-inhibited fibroblasts, Experimental cell research, 115, 1978, 37–46), etc. The ubiquitous cell-stimulating properties of Nys and other polyenes can be observed in all cell types—eucaryotes, bacteria and fungi. Nys stimulates all lymphocytes, the killer activity of the T cells, the macrophages, the polymorphonuclear neutrophils (PMN) the oxydative burst of the macrophages, etc. This universal cell-stimulating property of Nys could only be explained by way of the BP. Nys acts like a universal, biological ion channel and leads to cell stimulation by depolarization. This effect can be observed in all eucaryotes. The energetic mechanism of a cell stimulation by Nys is based on the universal equation of the BP: $E=E_A.f$ (see above). As in the physiological membrane proteins that are responsible for the ion transport across the membrane, for Nys, too, an open and a closed state could be observed for its ionophoric activity (Ermischkin L. N., et al., Single ionic channels induced in lipid bilayers by polyene antibiotics amphotericin B and nystatine, Nature 262, 1976, 698–9). From this it can be concluded that in Nys, too, the same quantum effects which are responsible for the formation of solitons bring about specific configurational changes of the Nys structure and thus dynamically control the opening of the Nys channels.

Nys stimulates most cells in concentrations between 5 and 50 µg/ml without triggering cell lysis. In very high concentrations Nys results in cell lysis (=apoptosis) due to an excess depolarization and dissipation of the LRC. Cell lysis, however, is observed only at very high concentrations of more than 100 µg/ml. In this case the incubation must be 24 hrs or more. Cell lysis increases with incubation time. During a short action time, however, cell lysis rarely occurs. The cells quickly recover after the excess stimulation. Resting cells are less sensitive to an excess depolarization by Nys than cells that have undergone an a priori maximum stimulation. This phenomenon, too, can be easily explained from an energetic point of view. Immune cells are resting cells and require maximum stimulation until they are activated. In the acute immune reaction, e.g., the concentrations of the cell-stimulating humoral factors such as the lymphokines in the body go up to the 10,000-fold. In contrast, the tubular cells of the kidneys are maximally stimulated under normal conditions. The i.v. administration of Nys, Amp or any other polyene macrolide leads very quickly to kidney toxicity even at very low concentrations. Therefore, Nys is not admitted i.v. This is in clear contrast to the excellent tolerance of Nys upon oral administration of very high doses (up to 5 g daily) over a prolonged period of time which was surprising found according to the invention.

This discrepancy in the safety profile between the oral and the systemic administration lead to the wrong conclusion that oral Nys is not resorbed. As evidence for this conclusion the low concentrations of nystatin in the serum after oral administration are mentioned. This conclusion is not admissible. Nys is a lipophilic substance and has a very high affinity to both cholesterol and its derivatives such as bile acid with which it forms micellae, and to biological membranes. In the presence of lipid membranes in ionic solution the entire Nys is membrane-bound. In the body the resorbed Nys immediately binds to the cell membranes—it is in the so-called deep compartments—and does not occur in the plasma which corresponds to an ionic solution. After i.v. administration of Nys the substance vanishes from the plasma within only few minutes and distributes in the deep compartments. The entire Nys in the plasma is bound to lipoproteins. However, the Nys concentration on the membranes of the blood cells has not been measured.

The kinetics of the polyene macrolides has been examined very insufficiently. There are only results for Amp available and the corresponding data are highly insufficient. The knowledge about the kinetics of i.v. Amp are based on the data of only 2 patients (A. J. Atkinson & J. E. Bennet, in Antimicrob. Agents & Chemoth. (1978), Vol. 13, p. 271–276). This invention, in contrast, is based, inter alia, on the surprising finding that polyenes, such as Nys and Amp upon oral and intranasal administration are substantially resorbed and evoke systemic therapeutical effects.

It was found according to the invention that oral Nys and Amp are resorbed by the gastrointestinal tract almost completely and are mainly stored in the liver but also in other mesenchymal and immunological organs. Due to its lipophilic properties oral Nys obviously bind to bile acid and is transported to the liver and other mesenchymal organs by the chylomicrons. This kinetic behavior is typical of most lipophilic substances (Koch & Ritschel, Synopsis der Biopharmazie und Pharmakokinetik, Ecomed, 1986). If the presently held belief were true that oral Nys is not or only insufficiently resorbed, the major part of Nys would have to be excreted together with the feces, for there is no indication so far that Nys is degraded in the gastrointestinal tract. However, we succeeded in finding that the share of Nys excreted daily with the feces is less than 1% of the orally taken daily dose. Since a degradation in the intestinal tract therefore has to be excluded, the only possibility remaining is that Nys is substantially resorbed by the intestinal tract.

The resorption of Nys and Amp could first be detected via their therapeutical effects. Since the bioavailability of lipophilic drugs cannot be ascertained via the serum concentration it is recommended that the systemic pharmacodynamic effects be ascertained, e.g. by the challenge and dechallenge method. Another possibility is the ascertainment of the strength of the effects in relation to the dose administered (dose-effect relation). A variety of challenge-dechallenge tests and tests with increasing doses in patients suffering from different diseases which respond to Nys and/or Amp was carried out. The average daily dose of Nys was 1 to 1.5 g in the challenge-dechallenge tests. In the tests with increasing doses a daily dose of from 250 mg and 2 g was used. Nys and Amp were administered orally as powders, in gelatin capsules a 250 mg pure substance. The results can be summarized as follows:

a) In menopausal women suffering from CFS (chronic fatigue syndrome) a dose-dependent increase in vaginal discharge after 1 to 2 weeks' treatment with 1 to 1.5 g Nys was observed. After dechallenge, the discharge ceased after 1 to 2 days and during challenge started again. An increase in discharge was observed only at a dose of 500 mg Nys or Amp.

b) Increase in bile secretion after 1 week treatment with Nys. Disappearance of sonographically detected gallstones in 4 patients after 2 months' therapy with 1.2 g Nys and in one patient with 1.5 g Amp after 3 months' therapy.

c) Increase in prostaglandin biosynthesis after 1 to 2 weeks' therapy with 1 to 1.5 g Nys or Amp.

d) Dose-dependent decrease in total cholesterol plasma levels in patients suffering from atherosclerosis after 2 to 8 weeks. The cholesterol-reducing effect occurs only at a daily dose of 500 mg and leads to a sustained decrease of cholesterol levels at a daily dose of 1 to 1.5 g Nys or Amp. Increase in cholesterol levels after dechallenge.

e) Remission of symptoms, such as allergic rhinitis, asthmatic attacks and food intolerances, in therapy-resistant allergies, such as allergies to dust mites, food allergies, etc., after 6 to 8 weeks' therapy with a daily dose of 1 g Nys or Amp.

f) Decrease of prostatic hypertrophy in old male patients after 3 to 6 months' therapy with 1 to 1.5 g Nys or Amp. Increase in hypertrophy about 3 months after termination of the therapy.

g) Improvement of the skin turgor after oral administration of Nys or Amp. Deterioration after dechallenge.

h) Lowering the mortality and infection morbidity (by stimulating the immune response) in intensive care patients suffering from severe multiple traumata after administration of 3 g Amp per day as oral paste, starting 24 hours after the traumata were inflicted.

i) Increase in body weight (5 to 10 kg) in final stage cachectic tumor patients after 2 to 4 weeks' therapy with 1.5 to 2 g Nys or Amp. Decrease in weight after discontinuation of the therapy by external physicians. Renewed increase when the therapy was resumed.

j) Dose-dependent remission (beginning at a daily dose of 1 g Nys or Amp) of the symptoms of CFS after 4 to 8 weeks. No dechallenge made.

Furthermore, kinetic tests were made with Nys. Four patients who had undergone cholecystectomy received one week prior to the operation and one week after the operation daily 1 g Nys orally. During the operation tissue samples from the bile walls, bile and liver were taken. During the first few postoperative days gall samples were taken from the T tube drainage. The tissue concentrations of Nys were from 80 and 180 $\mu$g/g in the liver, from 50 and 120 $\mu$g/g in the bile wall and from 30 and 150 $\mu$g/ml in the bile. These preliminary results agree with results from other kinetic studies, which, however, were carried out with i.v. Amp (Collette N. et al., in Antimicrob. Agents and Chemoth., 33, 1989, 362–68, R. M. Lawrence et al., in J. Antimicrob. Chemoth., 6, 1980, 241–49). These studies show that i.v. Amp is predominantly stored in the liver, bile and spleen. It can be assumed that the lipophilic polyenes after resorption from the gastrointestinal tract are mainly distributed in vital secondary immunological organs.

VII. Novel Clinical Indications for Polyene Macrolides

1. Virus Infections

Every virus particle enters the host cell by fusing with the host's cell membrane and by then releasing its particle content into the cell. In this process, viral membrane proteins remain in the host cell membrane and can be detected as markers. On the basis of the deliberations following from the BP, such virus proteins serve to control the viral genome in the DNA of the cell by the electromagnetic, delocalized coupling of the LRC and to thereby allow viral replication. This energetic coupling has not been recognized so far by genetics. If expression of such viral proteins in the host cell is suppressed, for instance by endocytosis, no viral replication takes place. Replication of the virus requires optimum conditions. In most cases, the viral DNA or RNA is degraded by repair mechanisms and the virus is metabolized in the cell. Only in one in about 10,000 cells which are infected by the HIV virus occurs replication. The effectivity of the repair mechanisms increases with the stimulation of the cells. The efficiency of all cell reactions including the repair mechanisms is increased by an enhanced depolarization of the cells. An increase in depolarization of virus-infected cells, however, also results in an increase in endocytosis of viral membrane proteins. Since they no longer emerge on the surface of the cells, no specific electromagnetic coupling to the proviral DNA takes place. This is a short explanation of the bioenergetic mechanism of virus replication in human cells. Two important conclusions can be drawn: a) during depolarization the viral membrane proteins disappear from the cell surface of infected cells and can no longer be measured as markers; during repolarization they are increasingly expressed; b) depolarizing substances have an antiviral effect because they promote endocytosis of the viral membrane proteins as well as the repair mechanisms in the infected cells and thus inhibit virus replication. These effects can be confirmed for Nys and other polyenes for all viruses examined so far.

a) AIDS

There is a detailed scientific report by Dr. med. G. Stankov on the AIDS etiology and its therapy with Nys (April 1995, Copyright DIAS Institut). It considers the most recent data of AIDS research until April 1995. The essential aspects of the development of AIDS and therapy of AIDS with Nys are briefly summarized in the following section:

The HIV membrane protein gp41-gp120 exhibits structural homology to MHC class II proteins which plays an important role in the MHC-restricted T-cell stimulation in the thymus. The interaction between the MHC molecule of the antigen-presenting cells (APC) and the T-cell receptor as well as other receptors of the CD type proceeds via their soliton triplets and leads both to direct depolarization as well as to the release of lymphokines to stimulate the immune cells involved. The HIV protein imitates the MHC molecule and uses the body's own immunostimulating mechanisms to control virus replication by electromagnetic coupling. CD4 is depleted because this T-cell subpopulation plays an important role in the MHC-restricted T-cell stimulation in the thymus and in the lymph nodes. Expression of gp41-gp120 results in an increase in apoptosis of the CD4 cells and is paramount for virus pathogenicity. gp41 corresponds to the transmembrane part of MHC, gp120 to the variable extracellular domain. gp120 changes under the bioenergetic constraint of the immune response. It quickly mutates when subjected to a virostatic (cell inhibiting) therapy and forms a one-step resistance. This is why it is impossible to develop a respective vaccine. Virus replication takes place during the entire duration of the disease. The AIDS-related complex represents only the last manifestation of the disease decompensation. At present, the patients are treated with AZT (ziduvodine) only in the last stage of the disease. According to the dipole model, AZT is a cell-inhibiting substance and increases the mortality of AIDS patients compared to placebo patients. The CONCORDE study, which examined the effect of ATZ in the early stage of HIV patients, confirms this conclusion within the meaning of the BP (Lancet, Vol. 343, 1994, 871–881). Presently, there is no effective therapy of AIDS.

A treatment with Nys and other polyene macrolides according to the model of the invention must inhibit both the expression of gp41-gp120 and the HIV replication in the infected cells. Nys and Amp inhibit in vitro the expression of gp120 and gp41 and p24 in H9 lymphocytes and suppress reverse transcriptase (Selvam M. P. et al. in AIDS Res. & Human Retrovirus, Vol. 9, 1993, 476–481). This in vitro study, however, does not indicate a possible HIV inhibition in vivo. Also, this study does not give any recommendation for a therapy with Nys or other polyenes in HIV patients since it was possible to explain the AIDS pathogenesis only when discovering the BP. Particularly, there is no indication in the art to chronically administer oral nystatin, in the high doses recommended by the invention, already after seroconversion to strengthen the immune system of HIV patients, since it was assumed that polyenes are not resorbed and since the cell-stimulating properties of Nys were not known. It is not known from the literature nor from practice that HIV patients were subjected to a therapy with Nys or another polyene in the early stage of the disease in order to suppress HIV replication by immunostimulation and to thereby prevent outbreak of the disease.

On the basis of the findings of the invention, HIV patients should be treated with polyene macrolides, such as Nys or Amp, preferably immediately after seroconversion. The therapy must be chronical for the duration of the disease. The recommended daily oral dose is about 0.5 to 5 g, preferably about 1 g to 3 g, particularly 1.5 to 2 g polyene macrolide as required.

The antiviral effect of polyene macrolides was confirmed by all viruses which have been examined so far in vitro. In the following, the observations made according to the invention are summarized.

b) Herpes Simplex Virus (HSV) Infections

Polyene macrolides, such as Nys and Amp, inhibit HSV I and HSV II in cell cultures at concentrations between 3 and 25 $\mu$g/ml. According to the invention, a rapid improvement of labial HSV infections after topical application of ointments (40 to 200 mg, preferably about 50 to 100 mg polyene macrolide/g ointment) is achieved. The drug must be administered several times. Depending on the concentrations of the active ingredient the ointment can be applied 3 to 10, preferably 5 to 8 times a day. A preferably chronic administration of oral macrolide may prevent recurrence of Herpes. The daily dose for chronic oral administration is in the range from about 0.5 to 5 g, preferably from about 1 to 3 g, preferably from 1 to 1.5 g.

c) Herpes Zoster Varicella (HZV) Infection

Polyene macrolides, such as Nys and Amp, inhibit HZV in cell cultures in concentrations between 3 and 25 $\mu$g/ml. After topical administration of highly-dosed ointments (about 40 to 200 mg Nys/Amp, preferably about 50 to 100 mg/g ointment) the efflorescences of shingles remit more rapidly than without therapy. The ointment may be applied several times a day, e.g., 3 to 6 times a day.

d) Hepatitis B Virus (HBV)

Polyene macrolides, such as Nys and Amp, inhibit dose-dependently the production of hepatitis B surface antigen (HbsAg) in human hepatoma cell line PLC/PRF/5.

After chronical oral administration of about 0.5 to 3 g, preferably about 1 to 1.5 g active ingredient daily, a remission of the symptoms and an improvement of the liver function can be achieved.

e) Vesicular Stomatitis (VS) Influenza and Reuscher Leukemia Virions

Polyene macrolides, such as Nys, Amp and filipin inactivate these virions in vitro.

f) Other Virus Infections: Nys inhibits in vitro Sindbis virus and vaccinia virus.

g) Recurrent Aphthous Stomatitis (RAS)

The pathogenesis of RAS is not clear, but there is substantial evidence that it can be triggered by various endogenous viruses. So far there has been no successful therapy for RAS. According to the invention, patients with RAS can be topically treated several times a day with a mucosa-adhering ointment that contains Nys, Amp or any other macrolide. For example, the treatment can be carried out in intervals of 1 to 3 hours 2 to 8 times a day. The content of the active ingredient of the ointment is in the range of from 20 to 200 mg, preferably of from 20 to 50 mg/g ointment. RAS remits after 24 to 48 hours (without therapy 5 to 7 days). The pain was relieved quickly after application of Nys.

h) On the basis of the above-mentioned data and the theoretical conclusions drawn from the BP it has to be assumed that polyene macrolides (topical and oral) are therapeutically effective also in the following virus infections, without, however, being limited to them:

Infections with picornaviridae (e.g., poliovirus), caliciviridae (e.g., Norwalk virus), togaviridae (e.g., Rubella virus), flaviviridae (e.g., yellow fever virus), coronoviridae, rhabdoviridae (rabies virus), filoviridae (Marburg virus), paramyxoviridae (German measles virus), orthomyxoviridae, bunyaviridae (e.g., California encephalitis virus), arenaviridae (lymphocytic choriomeningitis virus), reoviridae (e.g, rotavirus), retroviridae (e.g., HIV-1), hepadnaviridae (e.g., hepatitis A and hepatitis B virus), parvoviridae (e.g, human parvovirus B-19), papovaviridae (e.g., JG virus), adenoviridae (e.g., human adenovirus), herpesviridae, poxviridae, Epstein-Barr virus (e.g., infectious mononucleosis), cytomegalovirus.

2. Diseases with insufficient immune reaction, caused by a hereditary or acquired energetic impairment of the function of the MHC class I and II molecules and/or other integral proteins.

On the basis of the most recent experimental results it can be shown within the meaning of the BP that almost all chronic diseases are accompanied by an impaired immune system (see also diseases with immunopathogenesis, Harrison, Laws of Internal Medicine, McGraw Hill, 1992). Usually, these impairments are, as is evident from the deliberations according to the invention, impairments of the energy transmission of immunospecific membrane proteins. One either finds acquired mutations which relate to soliton-specific amino acids or hereditary variants, such as HLA alleles which occur significantly more frequently in certain diseases. Many diseases are associated with an impaired function of the MHC class I and II molecules. The defects frequently relate to the soliton-triplets of the peptide binding site for self-peptides or allo-peptides (HLA association, HLA=Human Leucocyte Association Antigen). This leads to an insufficient presentation of the antigens in the thymus and other secondary immune organs and to an insufficient cell-mediated (T cells) and humoral (B cells) immune response. The MHC-T-cell receptor interaction is energetically impaired and stimulation of the T-cells and B-cells (APC) is insufficient. The entire immune system is insufficient in terms of the energetic law since all immunospecific cell interactions are coupled to one another and are controlled via depolarization (e.g., growth, antibody production, phagocytosis, apoptosis, etc.) or repolarization (e.g., differentiation, chemotaxis, etc.). A detailed description of these complex immunological processes within the meaning of the BP must be omitted here. Individual examples of an HLA association are given below. Rheumatoid arthritis (RA) and multiple sclerosis (MS) are typical examples of chronic diseases with immunopathogenesis which can be put down to an impaired function of MHC class I and II molecules and of other integral proteins.

a) Rheumatoid Arthritis (RA)

A restricted set of genetically determined MHC class II molecules strongly predisposes to the development of RA. Increased risk for RA is associated with HLA-DR and especially with mutations of soliton-specific amino acids (Glu and Lys at position 70/71 on the HLA-DR$\beta$1 chain). Collagen arthritis and myelin-protein-induced experimental allergic encephalomyelitis show a close association with certain MHC class II molecules. The structure of MHC class II proteins has been recently elucidated (Nature, Vol. 368, 1994, 215–220). All 15 hydrogen bonds of the peptide binding site involve soliton-specific amino acids. Mutations of these amino acids which occur quite often in RA (HLA-DR association) lead to a deficient binding of peptides of the body's type II collagen which is incessantly built up and degraded in the bones. The collagen type II peptides are insufficiently presented to the T cells so that the self-tolerance to this collagen cannot be adequately developed. MHC class II molecules are essential for the MHC-restricted T-cell stimulation which is, as already pointed out above, mediated by depolarization. In RA, the activation of the T cells is insufficient leading to a cell-mediated autoreactivity to collagen. Hence, the RA pathogenesis is based on an energetic cause.

In RA, CD4 cells are found in large quantities at the site of inflammation. This is a frequent finding in many cell-mediated autoimmune diseases and clear evidence of the reduced efficiency of the T cell caused by insufficient stimulation. In contrast to the widely held belief in medicine the development of an autoreactivity is not an enhancement of the immune response which should be suppressed by cell-inhibiting drugs such as immunosuppressants but an energetically caused insufficiency of the involved immune cells which can be remedied with cell-stimulating drugs. Rheumatoid factors, mainly autoantibodies of the IgM isotype, are frequently found in RA patients. Ig production of synovial B cells exhibits an anti-type II-collagen activity. This clearly shows that the peptides of this collagen cannot be adequately bound and presented by the MHC class II molecules of the APC cells, particularly the B lymphocytes. This leads to the formation of insufficient T and B cells. Polyene macrolides, such as Nys and Amp, stimulate both the B and T cells by depolarization. Patients suffering from chronic RA which are treated according to the invention with, e.g., 1 g oral Nys/Amp daily, experience a clear and sustained improvement of the symptoms after about 1.5 to 3 months. Therapy is preferably chronic. The recommended dosage of the macrolide therefore amounts to about 0.5 to 4 g, preferably about 1 to 2 g/day, depending on the condition and progression of RA.

b) Multiple Sclerosis (MS)

MS is characterized by demyelination of the CNS, resulting from an inflammatory process. MS has an intermitting course. As in RA, CD4 cells and B lymphocytes can be found at the site of inflammation. Specific MHC class II alleles (Drw15 and Dqw6) are associated with an increased risk of MS and confirm the same finding as in RA: An insufficient binding of the body's peptides in certain HLA alleles leads to an impaired immune response. The result is also an autoreactivity to CNS proteins because self-tolerance cannot be adequately developed. Polyene macrolides, such as Nys and Amp (about 0.5 to 4 g, preferably about 1 to 1.5 g orally per day) clearly improve the MS symptoms in the patients and can even result in the disease being cured when administered in an early stage. A chronic therapy is preferred.

c) The two diseases, RA and MS, are representative of a group of diseases associated with an impaired function of MHC class I and class II molecules (HLA association) or other integral proteins. They exhibit the same energetically caused pathogenesis even if the symptoms may differ and may be found at different anatomical locations. All these diseases can be successfully treated by preferably chronic administration of oral Nys, Amp or another polyene macrolide. The daily dosage ranges from about 0.5 to 5 g, preferably about 1 to 2 g. For most diseases an HLA association is known. They are sub-classified anatomically (as far as possible, the corresponding HLA allele is indicated in brackets):

Bone diseases: ankylosing spondylitis (B27), Reiter's syndrome (B27), reactive arthritis in yersinia, salmonella or gonococcus (B27), psoriatic arthritis (B27, Bw38), juvenile rheumatoid arthritis (B27, Drw8), rheumatoid arthritis (Dw4, DR4), osteoarthritis.

Gastrointestinal diseases: gluten-sensitive enteropathy (DR3), other food-sensitive enteropathies, chronic active hepatitis (DR3), ulcerative colitis (B5, CD44), acute anterior uveitis (B27), Crohn's disease (CD44), liver cirrhosis.

Skin diseases: dermatitis herpetiformis (Dw3), psoriasis vulgaris (Cw6), pemphigus vulgaris (DR4, A10), Lichen ruber, Behcet's disease (B4), systemic lupus erythematosus (DR3), endogenous eczema and other forms of atopy (e.g., neurodermatitis), all forms of allergy, Sjögren syndrome (Dw3), dermatomyositis, scleroderma, chronic vasculitis (e.g., Raynaud's syndrome), diseases of the hair root.

Hematological diseases: idiopathic hemochromatosis (A3, B14), cold agglutinin disease, cryoglobulinemia, porphyria.

Endocrine diseases: type I diabetes mellitus (DR4, DR3, DR2, BfF1), hyperthyroidism (B8, Dw3), hyperthyroidism in Japanese (Bw35), adrenal insufficiency (Dw3), subacute thyroiditis de Quervain (Bw35), Hashimoto's thyroiditis (DR5), congenital adrenal hyperplasia (Bw47), distress syndrome, chronic fatigue syndrome, postmenopausal syndrome, primary and secondary amyloidosis, gout, cystic fibrosis.

Neurological diseases: myasthenia gravis (B8, DR3), multiple sclerosis (DR2), manic-depressive disorder (Bw16), schizophrenia (A28), polyneuroradiculitis (Guillain-Barre syndrome), polymyositis, slow-virus diseases of the CNS, other systemic diseases of the CNS (e.g., amyotrophic lateral sclerosis), Alzheimer's diseases.

Renal diseases: idiopathic membranous glomerulonephritis (DR3), Goodpasture's syndrome (anti-GBM, DR2), minimal change disease (B12), polycystic kidney disease (B5), IgA nephropathy (DR4).

Immunological infections: leprosy (B8), paralytic poliomyelitis (Bw16), IgA insufficiency (DR3), sarcoidosis.

3. Diseases with External and Internal Causes which are Associated with a Transitory or Chronic Immunoinsufficiency a) Sepsis:

In order to reduce the risk of sepsis, polyene macrolides, such as Nys or Amp, may be administered parenterally for selective decontamination of the digestive tract in intensive care patients after severe traumata. Tests have shown that Amp serves to reduce the mortality in these patients. The daily dosage is about 1 to 5 g, preferably about 2 to 4 g, particularly preferred about 3 g. The duration of therapy is several weeks, e.g., for the duration of the intensive care unit stay.

b) Immunodeficiency following Chronic Antibiotic Treatment:

Polyene macrolides, such as Nys or Amp, can be administered orally according to the invention to patients suffering from immunodeficiency and recurring infections caused by chronic administration of antibiotics. The infection rate can be reduced after a 6 week's to 3 month's therapy. The duration of the therapy is at least 6 months, at a dose of about 0.5 to 4 g, preferably about 1 to 1.5 g Nys or Amp/day.

c) Chronic Fatigue Syndrome (CFS):

The diagnosis of CFS was made after the CDC classification and is a frequent disease which is caused by external causes such as infections and administration of antibiotics as well as by internal causes (stress, hormone insufficiency, immunoinsufficiency). CFS is associated with a chronic immunodeficiency. The mutual influence of psychic, humoral and endocrinous factors such as can regularly be observed in CFS, is only explained by BP. All physiological factors have the same effector level: they regulate the cells by changing their membrane potentials. CFS is a classical indication of a therapy with polyene macrolides such as Nys or Amp (see also experimental part). According to the invention, CFS is treated with a daily dose of about 0.5 to 4 g, preferably about 1 to 2 g. The duration of treatment can be 3 to 6 months or longer.

d) Other diseases: any form of acquired or hereditary allergies that are associated with disorders of the respiratory system (e.g., rhinitis, asthma) or of the gastrointestinal tract (e.g., food-sensitive enteropathies).

4. Cancerous Diseases (Neoplasias of any Kind)

Cancer has four characteristic properties: a) it develops from single transformed cells (clonality); b) cell stimulation, growth and proliferation of the tumor cells elude the physiological supracellular regulation and are controlled by autostimulation (autonomy); c) there is no normal cell differentiation (anaplasia); d) the tumor cells can leave the cell aggregate and disseminate (metastasis).

All these phenomena can be energetically explained according to the invention. The mechanisms of quantum mechanics will be briefly explained. The transformation into carcinogenic cells is always a product of insufficient cell stimulation. Environmental toxins, such as nicotine, tar substances or asbestos (inhibition of the energy conversion along the membranes due to the dipole character of these carcinogens), chronic therapy with cell-inhibiting substances (e.g., with cyclosporin or other immunosuppressants) or radiation (direct energetic impact on the DNA and inhibition of the DNA solitons) result in a higher entropy in the cells. In all these cases the conversion of the LRC during an action potential is inhibited. An increased entropy leads to an increase in the degrees of freedom of the molecules in the cells ($dS=R.\ln Z_1:Z_2$). This holds also true for the transcription of the biological structures involved (DNA, RNA, DNA-controlling proteins, etc.). The probability increases that incorrect nucleotides are inserted and that mutations occur. Some of these mutations prove energetically advantageous for the cells. In many cancer cells a mutation-caused over-production of growth factors or receptors of growth factors, leading to an excess depolarization of the cell, can be observed. The result is an autostimulation of the cancer cells. In this manner the cancer cells become independent of supracellular regulation. The transformation into a cancer cell is always the result of insufficient cell stimulation and represents an evolutionary process (=adaptive process) of the cell at the expense of the self-organization of the organism. The over-production of growth factors or the transformation of protooncogenes into oncogenes is often the result of acquired mutations in the cancer cells, although genetically-inherited mutations can also contribute to the transformation. Usually, more than a single energetically caused modification (transformation threshold) is required for the cell to mutate. Cancer cells are, in contrast to the normal cells, immortal in vitro since their stimulation is autosufficient. The one-sided stimulation of the cancer cells results in a reduced differentiation and an increased endocytosis of integral proteins. Important membrane proteins, particularly those that are responsible for the formation of "tight junctions", do not emerge on the cell surface. The cancer cells lose their capability of adhering to neighboring cells and increasingly leave the cell aggregate. Due to the excess autostimulation they increasingly proliferate. However, the growth rate of cancer cells is often highly overestimated. Most cancer cells do not grow substantially faster than many normal body cells, they just grow in a more uncoordinated manner, beyond physiological supracellular regulation.

There are two possibilities of destroying cancer cells: by inhibiting the energy exchange on the plasma membrane or by apoptosis.

The first-mentioned mechanism is the only one presently used in cancer therapy. According to the dipole model, all cytostatics are potent cell-inhibiting substances which unspecifically inhibit both the healthy and the cancer cells. Since immune cells proliferate rapidly, the cytostatics substantially inhibit the immune system. The immune system is the strongest natural defense of the organism against the cancer cells. It controls the entire cell transformation and destroys above all the newly produced cancer cells. Since cancer cells are developed in our body with a certain degree of probability, an intact immune defense is an indispensable prerequisite for the prevention of cancer. Cytostatic therapy deliberately accepts a suppression of the immune defense.

The second, physiological mechanism used by the immune cells to destroy cancer cells is apoptosis. Immune cells can often be found in the vicinity of tumor cells. They increasingly produce lymphokines and other depolarizing or repolarizing substances and trigger apoptosis of the cancer cells by an excess de- or repolarization. They use for this purpose cell-bound proteins with which they enter into contact with the cancer cells (e.g., killer cells). Since the cancer cells are a priori more stimulated than the normal cells, the result is a selective apoptosis of the tumor cells.

The anticarcinogenic effect of the polyene macrolides according to the invention can thus be based on the following effects which may occur simultaneously:

The immune cells are stimulated by the macrolide. They increasingly destroy the cancer cells by apoptosis.

The macrolide directly stimulates the cancer cells and increasingly brings about their apoptosis by depolarization. This effect is particularly pronounced in liver metastases since the macrolide is stored in the liver in high concentrations. The macrolide results in a remission of the liver metastases. Presently, there is no drug available for the treatment of liver metastases.

The macrolide improves the supracellular regulation of healthy cells which are about to be transformed and thus prevents their transformation into cancer cells.

The macrolide stimulates all body cells and thereby strengthens the unspecific defense of the organism.

The treatment of cancer with the macrolides according to the invention is a fundamentally new approach which discards the conventional cytostatic therapy for being inappropriate and which is based on natural defense mechanisms. They result in the remission of metastases and clearly improve quality of life in patients suffering from solid tumors. There is evidence that life expectancy is substantially prolonged. They cannot cause large solid tumors to disappear completely. Therefore, a combination from surgical removal and medicamentous treatment with macrolides appears to be more promising than a purely medicamentous treatment. However, depending on the case, the operative risk has to be evaluated, too. The polyene macrolides will be paramount in cancer prophylactics. The sooner therapy with macrolides is started, the better the prognosis. Cancer therapy with macrolides, such as Nys or Amp, is preferably chronic. The daily dose is about 0.5 to 5 g, preferably about 1 to 3 g, depending on the patient's condition and the stage of the disease.

5. Wound Healing, Diseases with Impaired Wound Healing

The therapeutical effect of polyene macrolides, such as Nys and Amp, can be observed particularly well in the enhanced wound healing (predominantly after topical application). A rapid cell growth is caused by depolarization. In the same manner physiological healing is brought about. Any wound is surrounded by immune cells which energetically promote the growth of the damaged tissue cells by releasing stimulating lymphokines, eucosanoids and other humoral factors. Polyene macrolides, such as Nys and Amp, can be used according to the invention in high dosages (500,000 to 1,000,000 I.U./g basic ointment or, e.g., in 5 to 10% DSMO solution) several times a day, e.g., 3 to 8 times a day. Following diseases can be topically treated according to the invention with polyene macrolides, such as Nys and Amp (cf. experimental part):

any kind of wounds ulcus cruris decubitus or other chronic-trophic disorders burns. Burns must be immediately be treated with Nys. The effect can be observed within only few minutes. Nys prevents blisters. The administration of polyene macrolides, such as Nys, is particularly useful in the treatment of sun burn.

6. Diseases Caused by Disturbances of the Cholesterol Metabolism a) Atherosclerosis (AS) and Hypercholesterinemia The pathogenesis of AS has been unknown. There are several hypotheses and attempts at explanation which concentrate on individual known aspects of AS. The development of AS can only be correctly explained based on the teaching of the present invention. This explanation requires a correct understanding of the part cholesterol plays in the energy conversion along the biological membranes.

As already mentioned above, cholesterol is present in the membranes in a molar ratio of 1:1 to the other phospholipids which build the lipid bilayer. Its energetic function is to regulate the insulating properties of the membranes. The cholesterol molecule is almost apolar and is therefore a good insulator. Since the electric field strength of the membranes $F_E = 10^7$ Vm$^{-1}$ is very high, the cell membranes must exhibit excellent insulating properties as biological capacitors in order to build such strong electric field strengths. Any modulation of the dielectric properties of the membranes results in a modification of the plasma potential V and thus of the stored electrical energy $E_{el}$. As is known, the dielectric constant $\epsilon$ between the plates of a capacitor is inversely proportional to v and $E_{el}$. The modification of $\epsilon$ in the membranes allows infinitely many possibilities for influencing the energy conversion in the cells by modifying V and $E_{el}$. The biological regulation of the cell is based on this law. Cholesterol plays a decisive part in it. It is the universal biological regulator of $\epsilon$ in the membranes and thus also of the energy conversion in the cells. Therefore, its fundamental importance: on the one hand cholesterol is vital, on the other hand hypercholesterinemia results in several diseases and an increased mortality (the Janus molecule).

Cholesterol is exclusively produced by de-novo synthesis in the cells. Cholesterol is quickly metabolized in the lipid metabolism of the plasma membranes. The turnover rate of the cell membranes is extremely high. It is estimated that the lipid content of the membranes is regenerated completely within a few hours. Cell stimulation results in an increased membrane turnover. Any endocytosis of integral proteins is accompanied by, e.g., a consumption of lipid content (see, e.g., the inositol cascade). More than 95% of the cholesterol are located in the cell membranes. The cholesterol turnover takes place almost exclusively in the cell membranes and is proportional to the cell stimulation. The more cells are stimulated the more cholesterol they consume and the more cholesterol is newly produced in the mevalonic acid synthesis. This is because any cell stimulation leads to an adequate increase in all reactions in the cells via the LRC. The cell membranes can only take up certain amounts of cholesterol because its concentration determines the dielectric properties of the lipid bilayer. The excess cholesterol circulates in plasma or is stored in certain cells, e.g., in the macrophages, the so-called foam cells in the atheroma.

Cholesterol is transported in the body as LDL and VLDL. VDL and VLDL are large spherical particles that carry cholesterol and phospholipids in a ratio of 1:1 and contain apolipoproteins (apoA and apoE). apoA and apoE are polymorphous glycoproteins which interact with the apo receptors of the cells via their soliton triplets. The uptake of LDL and VLDL in the cell is coupled to its action potential or to the discrete potential fluctuations and increases during stimulation with depolarizing substances. Via this active energy transport the lipids are taken up by the cell. All cells have apo receptors. Liver cells have particularly many apo receptors because the uptake of alimentary fats and the de novo synthesis of cholesterol in the organism mainly takes place in this organ. Cholesterol is a precursor of steroid synthesis in the ovary, in the adrenal gland, in the prostate and in other endocrine and sexual organs. This fact is essential for the understanding of the therapeutical effect of Nys, Amp and other macrolides in prostate hyperplasia, postmenopausal syndrome, cholelithiasis and other diseases associated with disorders of the cholesterol metabolism.

Based on these facts, the development of AS can be explained logically and coherently. For energetic reasons, the cholesterol concentration in the membranes is maintained in a very narrow range. In this range the dielectric properties of the membranes and the energy conversion is optimal. The cholesterol metabolism is a very dynamic process which depends on the organism's whole metabolism. According to the universal equation of the BP the cholesterol metabolism directly depends on $E = E_A \cdot f$ (4). If the turnover is increased, more cholesterol is produced but there is no excess cholesterol in the body because it is increasingly consumed along the membranes. If the body's turnover—for whatever reasons—decreases, there is either an excess of cholesterol in the body—all the more so if more calories are taken up via the food than are consumed. This excess cholesterol cannot be taken up by the membranes and the cholesterol-storing cells and increasingly circulates in plasma (LDL and VLDL increase). If the supply is higher than the demand, cholesterol is deposited in the intima of the vessels. Here it is removed from the macrophages, the foam cells, and other immune cells. When the capacity of the immune system is exhausted, cholesterol is deposited in the intima. Atheromas are formed which lead to histologic degenerations of the vessels which are known for AS. This is the visible part of the AS pathogenesis. The consequences are hypertonia, coronary heart disease (CHD), ischemia, renal insufficiency, etc. The differences in metabolism are great between the individuals—there are faster and slower metabolizers among the population. The metabolic turnover is age-dependent and decreases in old age. Hypercholesterinemia is a particular disease of old age. But also other interindividual factors such as immobility are the cause for a predisposition. A reduced body turnover can also be genetically predisposed and can become manifest already in childhood. Familial hypercholestineremia (FH) is caused by hereditary mutations in the apoA and apoE receptors which, according to the most recent findings, relate to soliton-specific AS. LDL receptors in FH homozygotes do not bind sufficiently apoA and apoE. The lipid transport into the cell and thus energy conversion is reduced. Cholesterol accumulates in circulation. This excess causes AS in early childhood.

The therapy of AS can also be explained with the energetic law. Nys reduces the serum values of cholesterol in hypercholesterinemic patients via a global cell stimulation by depolarization. Particularly, the hepatocytes are stimulated: both the de-novo synthesis and the cholesterol consumption increase. The effect results in an increase in the cell frequency f according to the energy balance equation $E=E_A \cdot f$. According to the dipole model, all anticholesterolemics known from the art as MHG-CoA reductase inhibitors are cell-stimulating substances, such as Nys, however they have a less pronounced dipole character than the latter. Nys, Amp and other polyene macrolides according to the invention as well as the MHG-CoA reductase inhibitors result in an increase in MHG-CoA reductase (Goodman & Gilman, The Pharmacological Basis of Therapeutics, 1991, page 883) via a stimulation of the cells. At the same time, they enhance the cholesterol turnover in the cell membranes and thereby reduce the share of the circulating cholesterol. The anticholesterolemic effect can be observed with all lipid-lowering substances only after several weeks to months—the life-sustaining effects, such as reduction of mortality and sever cardiovascular events, however, only after 2 to 3 years (the Scandinavian Simvastatin Survival Trial, The Lancet, Vol. 344, Nov. 19, 1994, 1383–89). Patients suffering from hypercholesterinemia can be chronically treated according to the invention with an oral dose of about 0.5 to 4 g, preferably about 1 to 1.5 g of a polyene macrolide, such as Nys and Amp, per day. They show a substantial reduction of the overall cholesterol level after 1 to 2 months after start of the therapy. A lipid-reducing therapy therefore should preferably be chronic.

b) Alzheimer's Disease (Alz)

The apoE4 allele is significantly associated with Alz. This apolipoprotein is substantially involved in cholesterol metabolism. ApoE can be found in the plaques of dystrophic neuritis in Alz. apoE binds tightly to the soluble and insoluble forms of the β-amyloids in Alz patients. The amino acid position 112 (Cys) of the apoE allele is occupied by Arg+, which is a mutation variant which, as predicted theoretically, relates to a soliton-specific amino acid and causes an impaired energy conversion (The Lancet, Vol. 343, Apr. 23, 1994 and Sep. 18, 1993, page 697). Further mutations are also known. A chronic therapy with macrolides, such as Nys, improves the Alzheimer symptoms.

c) Prostatic Hyperplasia

The prostate is an important organ for the synthesis of sex hormones, with cholesterol functioning as precursor. A prostatic hyperplasia in old age reflects a reduced function of the organ. An organ hyperplasia typically develops compensatory if cell capacity of the organ is reduced (e.g., struma in iodine deficiency or hypothyreodism, adrenal hypertrophy in endocrinal insufficiency, etc.). Organ hyperplasias usually are reversible. Polyene macrolides, such as Nys and Amp, improve the energy turnover in the prostate and promote the cholesterol metabolism, thereby improving the production of steroid hormones. Remission of prostatic hyperplasia takes place after 3 to 6 months and is reversible—after termination of the Nys therapy, prostatic hyperplasia recurs within ½ to 1 year. This fact confirms the necessity of a chronic therapy with cell-stimulating substances for this and many other indications. The treatment according to the invention is carried out by administration of the active ingredient in a daily dose of about 0.5 to 4 g, preferably about 1 to 2 g.

d) Cholecystolithiasis (Gallstones)

Gallstones are caused by an insufficient production of bile acid. Bile acids are cholesterol derivatives with a stronger dipole character than cholesterol. They form micellae with the alimentary lipids in the gastrointestinal tract and thus facilitate their resorption. Nys stimulates the production of bile acids of the hepatocytes and leads to the degradation of gallstones. According to the dipole model, all effective cholagogics are cell-stimulating substances. The cholesterol acids chenodeoxycholic acid and ursodeoxycholic acid exhibit, e.g., due to the $COO^-$ group at the aliphatic part a stronger dipole character than cholesterol and are successfully used as drugs against cholecystolithiasis. The treatment according to the invention is carried out optionally by chronic administration of the active ingredient in a daily dose of about 0.5 to 4 g, preferably about 1 to 1.5 g.

e) Acne

Acne is closely associated with the cholesterol metabolism via the steroid hormone synthesis. Polyene macrolides, such as Nys and Amp, have a beneficial effect on acne both in topic and system application. Topical treatment is carried out by optionally repeated (2 to 4 times) application of an ointment (about 20 to 200 mg, preferably about 50 to 100 mg active ingredient/g of ointment). Oral treatment is carried out by daily administration of about 0.5 to 4, preferably about 1 g of the active ingredient.

7. Various Skin Diseases a) neurodermatitis b) dermatological allergies (contact allergies)

c) eczema d) psoriasis e) aphthous stomatitis f) any kind of stomatitis

In most of these diseases, the active ingredient must be administered both orally and topically (see experimental part).

VIII. Galenic Preparations for Polyene Macrolides

Depending on the specific indication the polyene macrolides according to the invention will be administered orally, topically or intranasally, e.g., as inhalation. Oral or topical administration is preferred.

According to the invention, the oral daily dose of the active ingredient will be in the range of about 1 to 200 mg/kg body weight, preferably about 10 to 100 mg/kg body weight, particularly preferred about 15 to 30 mg/kg body weight. The specific daily dose depends on the active ingredient used, the disease and the patient's condition and must be chosen by the attending physician. The preferred oral daily dose for adults for Nys and Amp is about 100 mg to 5 g, particularly about 0.7 to 2 g, e.g., 1.0 to 1.5 g. The maintenance dose of Nys and Amp is about 200 mg to 2 g. The frequency of application will be 1 to 6 times per day and preferably should be 1 to 4 times per day. 1 mg nystatin corresponds to about 5,000 I.U.

Appropriate preparations include tablets, capsules, lozenges, powder for emulsions, solutions and suspensions. Care is taken that all preparations contain the polyene as pure active ingredient. The share of other ingredients will preferably be minimal. For example, the tablets may contain other galenic ingredients such as ethyl cellulose, lactose, corn starch, magnesium stearate, talc, saccharose, paraffin, gelatin, wax, vanillin, etc. Lozenges may contain flavors, d-mannitol, polyvinyl alcohol or other alcohols, magnesium stearate, talc, etc. Capsules will, if possible, contain only the pure substance. All other necessary additives are reduced to a minimum. In emulsions conventional emulsifiers will be used. Dimethylsulfoxide (DMSO) can for instance be used for preparing solutions.

Topical applications will include the polyene macrolide in a dose of about 10 to 200 mg, preferably about 40 to 200, 50 to 100 mg/g of composition are particularly preferred. Examples of topical preparations include creams, ointments, pastes, lotions, emulsions, solutions, etc. The following additives may be used: soft and liquid paraffins, cetyl or stearyl alcohol and other alcohols, stearic acid, sorbic acid, sodium hydroxide, propyl and methyl hydrobenzoate, propylene glycol, glyceryl monostearate, scents, solvents such as DSMO, etc.

For inhalations with aerosol and nasal sprays appropriate inhalation solutions will be used. The concentrations of the polyene will be between 2 and 200 µg/ml, preferably about 10 to 20 µg/ml of the composition.

The compositions to be applied topically and intranasally may be applied 1 to 8 times per day.

Commercial Nys contains two components designated as nystatin A1 and nystatin A2. Nystatin A1 is considerably more stable than A2 and the ratio of A1 to A2 determines the stability of the material. Although not critical for the present invention, a commercial preparation is preferred which shows suitable stability. The choice of suitable commercial preparations is a routine matter for the person skilled in the art.

IX. Experimental Part

EXAMPLE 1

Treatment of AIDS Patients

At present, 3 HIV-positive symptom-free patients receive chronic oral Nys treatment (1.5 to 2 g/day). More patients are being recruited. 4 more patients with the AIDS-related complex (ARC) not showing systemic mycoses receive the same therapy. These patients showed an improvement of the ARC-symptoms after receiving treatment for 4 to 6 weeks.

The same results were obtained in 4 patients (2 without symptoms, 2 in the ARC phase) with a corresponding Amp treatment.

EXAMPLE 2

Treatment HSV Infections a) 25 patients suffering from *Herpes labialis* were topically treated with Nys ointment (50 mg Nys/g ointment) immediately after occurrence of the disease. Application frequency: 6 to 8 times a day. Relief from pain and remission of the pustulae was achieved within 24 to 28 hours. Treatment up to curing took 1 week.

The same results were obtained in 8 patients with a corresponding Amp treatment.

b) 7 patients with chronic recurrent HSV (3 to 4 HSV episodes per year) were prophylactically treated with orally administered Nys (1 g/day) for 3 to 6 months. The rate of incidence could be markedly lowered. 6 patients did not suffer from episodes for 6 months and more. 1 patient experienced a HSV infection only once and this was a mild form.

The same results were obtained in 5 patients with a corresponding Amp treatment.

EXAMPLE 3

Treatment of Herpes Zoster Varicella (HZV)

3 patients, including 2 children, suffering from HZV infections and shingles at the trunk were topically treated with Nys ointment (50 to 100 mg Nys/g ointment) for the duration of the disease. An intraindividual comparison with all patients showed a more rapid and marked remission of the efflorescences that had been treated as compared to sites that had not been treated.

The same results were obtained in 4 patients with a corresponding Amp therapy.

EXAMPLE 4

Treatment of Hepatitis B Virus (HBV) Infections 4 patients with chronic hepatitis B were treated with oral doses of Nys (1 to 1.5 g/day) for 6 months. Complete remission of the symptoms could be obtained. The liver values (GPT, GOT, gamma-GT) were back to normal towards the end of the treatment.

The same results were obtained with a corresponding Amp treatment.

EXAMPLE 5

Treatment of Recurrent Aphthous Stomatitis (RAS)

18 patient with RAS were treated with mucosa-adhering Nys ointment (20 to 50 mg/g of ointment) prepared according to the German patent application P 44 34 929.7. The ointment was applied every 2 hours. Pain was already markedly relieved after the first application. Depending on the size of the lesion, RAS disappeared within 24 to 48 hours, while RAS not being treated took 5 to 7 days to disappear. None of the patients showed RAS after a four-day therapy.

The same results were obtained in 12 patients with a corresponding Amp treatment.

EXAMPLE 6

Treatment of Rheumatoid Arthritis (RA) and Osteoarthritis (OA)

9 patients with chronic RA and 3 patients with OA were treated with oral doses of Nys (1 g/day). The RA symptoms disappeared after 6 to 8 weeks and did not reappear during the maintenance therapy (same dose). In 2 female patients therapy was temporarily discontinued and the symptoms reappeared. After the Nys treatment was resumed, the RA symptoms disappeared again (challenge-dechallenge).

The same results were obtained in 5 patients with a corresponding Amp treatment.

EXAMPLE 7

Treatment of Multiple Sclerosis (MS)

3 patients with MS received chronic treatment with oral doses of Nys (1 g/day). A marked improvement of the symptoms was observed as early as 2 months after commencement of therapy.

The same results were obtained in 2 patients with a corresponding Amp treatment.

EXAMPLE 8

Treatment of Allergies a) 7 patients with food allergies (3 with gluten-sensitive enteropathy, 2 with milk allergy and 2 with fruit allergies) were treated with daily oral doses of 1 g Nys for 6 months.

The intolerance phenomena largely disappeared after 2 to 3 months and the patients could eat the respective food.

The same results were obtained in 5 patients with a corresponding Amp therapy.

b) 15 patients with pollen allergies and 8 patients with dust allergies were treated with daily oral doses of 1 g Nys for 6 months. Before commencement of therapy, the allergies of all patients had resisted treatment for at least 5 years or since birth. In all patients an almost complete disappearance of the symptoms (allergic rhinitis, asthma attacks, blocked nose, etc.) could be seen after 6 to 8 weeks. After discontinuance of therapy for experimental purposes (dechallenge) the symptoms slowly reappeared in about half the patients. After resumption of therapy (challenge) the symptoms could again be cured/improved.

The same results were obtained in 7 patients with a corresponding Amp therapy.

EXAMPLE 9

Treatment of Morbus Crohn and Ulcerative Colitis

Both diseases show CD44-mutants in the crypts of the mucosa. CD44 takes part in the MHC-restricted T-cell-receptor interaction. 1 patient with morbus Crohn and 2 patients with ulcerative colitis received chronic treatment with oral doses of 1 to 1.5 g Nys/day. Progression of the disease could be stopped and the symptoms disappeared. Endoscopic investigations confirmed these findings.

The same results were obtained with a corresponding Amp therapy (2 patients with morbus Crohn, 1 patient with ulcerative colitis).

EXAMPLE 10

Treatment of Psoriasis 4 patients suffering from therapy-resistant psoriasis on the entire body, whose condition had remained unchanged for many years received chronic treatment with oral doses of 1 to 1.5 g Nys/day. In addition, Nys was applied topically. All patients showed improvement after 2 to 3 months. Remission of the marginal inflammation and reduction of the efflorescences was noted. There was a remission of hyperkeratosis within the psoriasis efflorescences and normal epithelialization isles formed. Scales and itching diminished after treatment for 3 to 4 weeks.

The same results were obtained in 2 patients with a corresponding Amp treatment.

EXAMPLE 11

Treatment of Liver Cirrhosis 3 patients with alcohol-induced liver cirrhosis received chronic treatment with oral doses of 1 to 1.5 g Nys/day. Their liver values and general well-being improved.

The same results were obtained in 4 patients with a corresponding Amp therapy.

EXAMPLE 12

Treatment of *Lichen ruber*

2 patients with *Lichen ruber* were treated with oral doses of 2 g Nys/day for 3 months. The efflorescences disappeared completely.

EXAMPLE 13

Treatment of Neurodermatitis 8 children with atopic neurodermatitis were topically treated with Nys ointment (20–50 mg/g of ointment). The ointment was applied 3 to 6 times a day. The neurodermatitis sites that were treated, were completely healed after a few days (3 to 7 days). By contrast, the efflorescences that were not treated persisted.

The same results were obtained in 5 children with a corresponding Amp therapy.

EXAMPLE 14

Treatment of Cold Hemagglutinin Disease (CHD)

1 female patient with chronic CHD and a very high level of monoclonal IgM antibodies was orally treated with 1 to 1,5 g Nys/day for 6 months. Acrocyanosis, which regularly already appeared at 16° to 18° C. of air temperature, largely disappeared. Intensity decreased and exposure time at temperatures below 16° C. increased. Contrary to the condition before treatment, acrocyanosis could not be produced in repeated provocation tests with cold water. Moreover, the antibody level was lowered as well.

EXAMPLE 15

Treatment of Polyneuroradiculitis (Guillain-Barre Syndrome)

1 patient with polyneuroradiculities and neurological pareses received chronic treatment with oral doses of 1 g Nys/day. The pareses and pain symptoms clearly diminished.

EXAMPLE 16

Prophylactic Treatment of Sepsis 405 intensive care patients suffering from grave multiple traumata were orally treated with 3 g/day amphotericin B or Nys for the duration of intensive care (2 to 6 weeks). Compared to the standard group without therapy, the mortality and morbidity rate of nosocomial infections could be lowered in these patients. As the patients showed no mycoses, these effects are to be attributed to the immunostimulation by the polyenes.

EXAMPLE 17

Treatment of Immunodeficiency after Chronic Administration of Antibiotics 9 patients that had been chronically treated with antibiotics for diverse infections and showed reduced immune response received oral doses of 1 to 1.5 g Nys/day over a period of 3 to 6 months. None of the patients showed a mycosis. In this period, the therapy with antibiotics was discontinued. During and after the Nys treatment the conditions of the patients improved significantly with the result that a further treatment with antibiotics became unnecessary. The infection rate dropped and the immunological parameters went back to normal.

The same results were obtained in 5 patients with a corresponding Amp treatment.

EXAMPLE 18

Treatment of Chronic Fatigue Syndrome (CFS)

12 patients with CFS according to the CDC classification were orally treated with 1 to 1.5 g Nys/day for 3 to 6 months. In 8 patients the CFS syndrome disappeared completely and in the other 4 patients the symptoms were clearly improved as was their well-being.

The same results were obtained in 7 patients with a corresponding Amp therapy.

EXAMPLE 19

Treatment of Postmenopausal Syndrome (PMS)

5 patients with PMS who had not been treated with hormones underwent treatment with 1 g Nys/day during 3 to 6 months. The PMS symptoms disappeared completely.

The same results were obtained in 3 patients with a corresponding Amp therapy.

EXAMPLE 20

Treatment of Cancer a) 3 patients with pancreas carcinoma and distant metastases (liver and lymphatic nodules) and cachexia were orally treated with 1.5 to 2 g Nys/day. Remission of the liver metastases was observed in 1 patient (confirmed by radiographs). All 3 patients showed weight increases and their well-being improved noticeably after only 2 weeks of treatment. In 1 patient, the Nys therapy was replaced with chemotherapy and radiotherapy. The patient died shortly afterwards. The 2 other patients continued to received the Nys therapy and have already reached an age above the statistical age.

b) 4 patients with carcinoma of the breast who had undergone ablation received chronic treatment with oral doses of 1 to 1.5 g Nys/day. No metastatic formation was noted.

The same results were obtained with a corresponding Amp therapy (1 patient with pancreas carcinoma, 4 patients with carcinoma of the breast).

c) Two patients with oat-cell lung carcinoma in the final stage and cachexia were treated with 1.5 to 2 g Nys. It was possible to stop the cachexia.

d) 1 patient with liver carcinoma and cachexia was orally treated with 1.5 to 2 g Amp/day. There was a remission of the liver metastases (detected by radiographs). The patient showed a weight increase and a distinct improvement in his well-being after only 2 weeks of treatment.

e) 3 patients with colon cancer (Duke's carcinoma) in the final stage and cachexia were orally treated with 1.5 to 2 g Amp/day. Distinct relief from the gastrointestinal symptoms could be brought about and cachexia could be stopped.

EXAMPLE 21

Use of Nys in Wound-healing 32 patients with soft tissue wounds were topically treated with Nys ointments (50 to 100 mg Nys per g of ointment). The ointment was applied several times a day. An intraindividual comparison with wounds that had not been treated showed a significantly faster healing. The healing time could be reduced with Nys by 35 to 50%.

The same results were obtained in 14 patients with a corresponding Amp therapy.

EXAMPLE 22

Treatment of Burns a) 19 patients with second degree and third degree skin burns were treated with Nys ointment immediately after suffering the burns. The ointment was applied 6 to 8 times per day. Nys prevents the formation of blisters and brings relief from pain within few minutes. Nys prevents the formation of cicatrices and accelerates healing. The Nys ointment must be applied several times a day.

b) Several persons with sun burns were also topically treated with Nys ointment. The sun burns disappeared completely within 24 to 48 hours.

The same results were achieved with a corresponding Amp therapy (14 patients with wounds, 11 with burns, several ones with sun burns).

EXAMPLE 23

Treatment of Ulcus Cruris and Decubitus 8 patients with chronic ulcus cruris and 9 patients with decubitus were topically treated with Nys. The medication was topically applied 3 to 6 times per day. Depending on their size, the open wounds were epithelized almost completely after about 2 to 4 weeks. After discontinuance of therapy, relapses occurred. Therapy was continued chronically.

The same results were obtained with a corresponding Amp treatment (3 patients with ulcus cruris, 5 patients with decubitus).

EXAMPLE 24

Treatment of Hypercholesterinemia

Both the sepsis study (see example 16) and the individual explorative studies showed markedly lower levels of total cholesterol and LDL fraction in a number of hypercholesterinemic patients that had been treated with oral doses of 1 to 2 g Nys/day. HDL remained unchanged. A decrease occurred after 10 to 14 days, in some patients only after 3 to 4 weeks. The higher the initial value of plasma cholesterol, the greater the lipid-lowering effect of Nys. In patients with reduced cholesterol values (for instance after severe traumata), cholesterol was found to increase. Nys puts the cholesterol metabolism in the body back to normal.

The same results were obtained with a corresponding Amp therapy.

EXAMPLE 25

Treatment of Prostatic Hyperplasia 6 patients with prostatic hyperplasia were orally treated with 1 mg Nys/day for at least 6 months. Hyperplasia already started to progressively disappear after 3 months. The urea flow improved.

The same results were obtained in 4 patients with a corresponding Amp therapy.

EXAMPLE 26

Treatment of Gallstones

In 4 patients with sonographically ascertained cholecystolithiasis, who were orally treated with 1 to 1.5 g Nys/day, gallstones could no longer be detected (by sonography and in radiographs with X-ray contrast agents) at the end of therapy.

The same results were obtained in 1 patient with a corresponding Amp treatment.

EXAMPLE 27

Treatment of Acne

Several patients with acne, including acne conglobata, were treated topically with Nys ointment (20 to 100 m g Nys/g ointment) and orally with Nys (1 g/day). It was possible to achieve a marked acne remission.

The same results were obtained with a corresponding Amp therapy.

The daily doses indicated in the present description can be administered depending on the individual case, either as a single dose or divided into several partial doses, for instance 2, 3 or 4 partial doses, for example before or after the meals.

The term "chronic administration" as used herein includes both lifetime administration of the active ingredient and the administration up to a possibly permanent disappearance or remission of symptoms. Depending on the severity of the disease, the symptoms can disappear in the course of the chronic therapy of the invention, for instance within 3 to 6 months, sometimes earlier, but in many cases only later, for instance within 12 months. It may furthermore include an intermittent chronic therapy, such as for instance a therapy for 3 to 6 months, followed by a therapy pause for 6 to 12 months or resumption of the therapy when the disease reappears.

A therapy according to the invention usually begins once the macroscopic or histological findings are available. In special cases, for instance in the treatment of AIDS or cancer, early therapy is preferred. Early therapy should begin immediately after the diagnosis is made (for instance by immunological evidence) but before the availability of macroscopic or histological findings. In the case of a known predisposition, for instance due to age or hereditary factors, a prophylactic chronic administration of polyene macrolides is also conceivable.

Starting from the general teaching given in the description and on the basis of the specific teaching of the examples, a person of average skill in the art can select other suitable polyene macrolides as therapy for the afore-mentioned indications, without this requiring him to make inventive efforts of his own.

TABLE 1

Tetraenes

| Compound | Microorganism | Aggregated product |
|---|---|---|
| Amphotericin A | S. nodosus | $C_{46}H_{73}NO_{19}$ |
| Arenomycin B | A. tumemacerans var. griseoarenicolor | $C_{36}H_{55}NO_{13}$ |
| Aureofusein | S. aureofuscus | $C_{28}H_{43}NO_{12}$ |
| Lucensomycin (Etruscomycin) | S. lucensis | $C_{36}H_{53}NO_{13}$ |
| Nystatin $A_1$ (Fungicidin) | S. noursei | $C_{47}H_{75}NO_{17}$ |
| Nystatin $A_3$ | S. noursei | $C_{35}H_{85}NO_{20}$ |
| Pimaricin | S. natalensis | $C_{33}H_{47}NO_{13}$ |
| Plumbomycin A | A. plumbeus | $C_{47-48}H_{85-87}NO_{20}$ |
| Plumbomycin B | A. plumbeus | $C_{46-47}H_{78-82}NO_{20-21}$ |
| Polifungin B | S. noursei | $C_{47-48}H_{75-79}NO_{18}$ |
| Protocidin | Streptomyces sp. | $C_{29}H_{45}NO_{13}$ |
| Rimocidin | S. rimosus | $C_{39}H_{61}NO_{14}$ |
| Tetrafungin | S. albulus subsp. tetrafungini | $C_{47}H_{82}NO_{23}$ |
| Tetramycin A (Tetramycin) | S. noursei var. jenensis | $C_{35}H_{53}NO_{13}$ |
| Tetramycin B | S. noursei var. jenensis | $C_{35}H_{53}NO_{14}$ |
| Tetrin A | Streptomyces sp. | $C_{34}H_{51}NO_{13}$ |
| Tetrin B | Streptomyces sp. | $C_{34}H_{51}NO_{14}$ |
| Toyamycin | S. toyamaensis | $C_{41}H_{65}NO_{18}$ |
| A-435 | S. rimosus | $C_{31-34}H_{44-51}NO_{13-14}$ |
| A-5283 | | $C_{31-34}H_{44-51}NO_{13-14}$ |
| PA-166 | Streptomyces sp. | $C_{35}H_{53}NO_{14}$ |

TABLE 2

Pentaenes

| Compound | Microorganism | Aggregated product |
|---|---|---|
| Aurenin | Actinomyces aureorectus | $C_{33}H_{54}O_{11}$ |
| Capacidin | Streptomyces sp. | $C_{54}H_{85}N_2O_{18}$ |
| Chainin | Chainia minutisclerotica | $C_{33}H_{54}O_{10}$ |
| Elizabethin | S. elizabethii | $C_{35}H_{58}O_{12}$ |
| Filipin I | S. filipinensis | $C_{35}H_{58}O_9$ |
| Filipin II | S. filipinensis | $C_{35}H_{58}O_{10}$ |
| Filipin III (Hauptkomponente) | S. filipinensis | $C_{35}H_{58}O_{11}$ |
| Filipin IV | S. filipinensis | $C_{35}H_{58}O_{11}$ |
| Fungichromin | S. cellulosae S. roseoluteus S. fradiae S. griseus | $C_{35}H_{58}O_{12}$ |
| Homochainin | C. minutisclerotica | $C_{34}H_{56}O_{10}$ |
| Kabicidin | S. gougerotii | $C_{35}H_{60}O_{13}$ |
| Lienomycin | Actinomyces diastatochromogenes var. lienomycini | $C_{67}H_{107}NO_{18}$ |
| Moldcidin A | S. griseofuscus | $C_{42}H_{81}NO_{19}$ |
| Norchainin | Chainia minutisclerotica | $C_{32}H_{52}O_{10}$ |
| Onomycin-I | Streptomyces sp. | $C_{43}H_{76}NO_{17}$ |
| Pentacidin | A. hygroscopicus | $C_{31}H_{50}O_{10}$ |
| Pentafungin | S. antimycoticus | $C_{41}H_{74}NO_{16}$ |
| PA-153 | Streptomyces sp. | $C_{37}H_{61}NO_{14}$ |
| S 728 | Streptomyces sp. | $C_{56}H_{93}NO_{20}$ |

TABLE 3

Hexaenes

| Compound | Microorganism | Aggregated product |
|---|---|---|
| Candihexin A | Streptomyces viridoflavus | $C_{48}H_{76}NO_{19}$ |
| Candihexin B | S. viridoflavus | $C_{48}H_{90}NO_{21}$ |
| Cryptocidin | Streptomyces sp. | $C_{52}H_{84}NO_{17}$ |
| Grecomycin | S. chromogenes var. graecus | $C_{38}H_{41}O_{10}$ |

TABLE 4

Heptaenes

| Compound | Microorganism | Aggregated product |
|---|---|---|
| Acmycin | Streptomyces sp. | $C_{38}H_{68}NO_{30}$ |
| Amphotericin B | S. nodosus | $C_{47}H_{73}NO_{17}$ |
| Aureofungin A | S. cinnamoneus var. terricola | $C_{59}H_{86}N_2O_{19}$ |
| Aureofungin B | S. cinnamoneus var. terricola | $C_{57}H_{85}NO_{19}$ |
| Candidin | S. viridoflavus | $C_{47}H_{71}NO_{17}$ |
| Flavumycin A | Actinomyces flavus var. geptinicus | $C_{60}H_{91}N_2O_{17-19}$ |
| Hamycin | S. pimprina | $C_{58}H_{86}N_2O_{19}$ |
| Levorin $A_2$ | A. levoris | $C_{59}H_{89}N_2O_{18}$ |
| Levorin B | A. levoris | $C_{62}H_{98}N_2O_{25}$ |
| Lucknomycin | S. diastatochromogenes | $C_{61}H_{98}N_2O_{24}$ |
| Partricin A | S. aureofaciens | $C_{59}H_{86}N_2O_9$ |
| Partricin B | S. aureofaciens | $C_{55}H_{84}N_2O_{19}$ |
| Perimycin A | S. coelicolor var. aminophilus | $C_{59}H_{88}N_2O_{17}$ |
| Trichomycin A | S. hachijoensis | $C_{61}H_{86}N_2O_{21}$ |
| AF-1231 | Streptomyces sp. | $C_{42}H_{68}N_2O_{17}$ |
| DJ-400 $B_1$ | S. surinam | $C_{65}H_{96}N_2O_{21}$ |
| DJ-400 $B_2$ | S. surinam | $C_{58}H_{86}N_2O_{20}$ |

TABLE 4-continued

Heptaenes

| Compound | Microorganism | Aggregated product |
|---|---|---|
| 67-121A | *Actinoplanes caeruleus* | $C_{59}H_{88}N_2O_{19}$ |
| 67-121 C | *Actinoplanes caeruleus* | $C_{65}H_{98}N_2O_{28}$ |

I claim:

1. A method for modulating the energy conversion in the body cells of a mammal, comprising the oral, topical and/or intranasal administration to the mammal, of at least one polyene macrolide or functional derivative thereof in an amount influencing the frequency of variations in the cellular potential.

2. A method for treating a disease comprising the topical, oral and/or intranasal administration of a therapeutically effective amount of at least one polyene macrolide or a functional equivalent thereof to a mammal suffering from said disease wherein said disease is not caused by a fungus.

3. A method for treating HIV infections, wherein after the diagnosis of seroconversion and preferably before the manifestation of AIDS symptoms the polyene macrolide is given to a HIV-infected patient by chronic oral administration.

4. The method according to claim 3, wherein the polyene macrolide is administered in a daily dose of about 0.5 to 5 g, preferably about 1 to 3 g.

5. The method according to claim 2 for treating herpes simplex virus infections, wherein the polyene macrolide formulated into a suitable pharmaceutical composition having an active ingredient content of about 40 to 200 mg per g of the composition is applied several times daily onto the inflammation focus until the symptoms disappear; and/or the polyene macrolide is chronically administered in a daily oral dose of about 0.5 to 5 g.

6. The method according to claim 2 for treating varicella zoster infections, wherein the polyene macrolide formulated into a suitable pharmaceutical composition having an active ingredient content of about 40 to 200 mg per g of the composition is applied several times onto the inflammation focus until the efflorescences disappear.

7. The method according to claim 2 for treating hepatitis B virus infections, wherein the polyene macrolide is orally administered in a daily dose of about 0.5 to 3 g over a period of about 3 or 6 months or more until the symptoms disappear.

8. The method according to claim 2 for treating recurrent aphthous stomatitis, wherein the polyene macrolide formulated into a suitable pharmaceutical composition having an active ingredient content of about 20 to 200 mg/g of the pharmaceutical composition is applied onto the lesions optionally several times a day until the lesions disappear.

9. The method according to claim 2 for treating rheumatoid arthritis, osteoarthritis or other rheumatic diseases, wherein the polyene macrolide is orally administered to the patient in a daily dose of about 0.5 to 4 g until the symptoms disappear.

10. The method according to claim 2 for treating multiple sclerosis, wherein the polyene macrolide is chronically administered to the patient in a daily oral dose of about 0.5 to 4 g.

11. The method according to claim 2 for treating food allergies, wherein the polyene macrolide is chronically administered to the patient in a daily oral dose of about 0.5 to 4 g.

12. The method according to claim 2 for treating allergies, such as pollen, dust, mite and food allergies and the like, wherein the polyene macrolide is chronically administered to the patient in a daily oral dose of about 0.5 to 4 g.

13. The method according to claim 2 for treating liver cirrhosis wherein the polyene macrolide is chronically administered to the patient in a daily oral dose of about 0.5 to 4 g.

14. The method according to claim 2 for treating *Lichen ruber*, wherein the polyene macrolide is orally administered to the patient in a daily dose of about 1 to 4 g until the efflorescences have disappeared completely.

15. The method according to claim 2 for treating neurodermatitis, wherein the polyene macrolide formulated into a suitable pharmaceutical composition having an active ingredient content of about 20 to 200 mg/g of the composition is applied onto the affected skin portions several times a day until the symptoms have disappeared completely.

16. The method according to claim 2 for treating the cold agglutinin disease, wherein the polyene macrolide is chronically administered to the patient in a daily oral dose of about 0.5 to 4 g.

17. The method according to claim 2 for treating polyneuroradiculitis, wherein the polyene macrolide is chronically administered to the patient in a daily oral dose of about 0.5 to 4 g until the pareses and the pain symptoms disappear.

18. A method according to claim 2 for prophylactically treating sepsis, wherein the polyene macrolide is orally administered to the patient in a daily dose of about 1 to 5 g.

19. The method according to claim 2 for treating immunological disorders produced by antibiotics, wherein the polyene macrolide is chronically administered to the patient in a daily oral dose of about 0.5 to 4 g.

20. The method according to claim 2 for treating the chronic fatigue syndrome, wherein the polyene macrolide is orally administered to the patient in a daily dose of about 0.5 to 4 g until the symptoms have disappeared completely.

21. The method according to claim 2 for treating the postmenopausal syndrome, wherein the polyene macrolide is orally administered to a patient in a daily dose of about 0.5 to 4 g until the symptoms have disappeared completely.

22. The method according to claim 2 for treating cancer, wherein the polyene macrolide is chronically administered to a patient in a daily oral dose of 0.5 to 5 g.

23. The method according to claim 2 for treating soft-tissue wounds, wherein the polyene macrolide formulated into a suitable pharmaceutical composition having an active ingredient content of about 50 to 200 mg/g of the pharmaceutical composition is applied optionally several times a day to the affected site until the wounds have healed.

24. The method according to claim 2 for treating burns, including sun burn, wherein the polyene macrolide formulated into a suitable pharmaceutical composition having an active ingredient content of about 50 to 200 mg/g of the composition is applied optionally several times a day until relief from the symptoms is brought about.

25. The method according to claim 2 for treating ulcus cruris and decubitus, wherein the polyene macrolide formulated into a suitable pharmaceutical composition is applied to the lesion in a concentration of about 50 to 200 mg/g of the applied composition until healing is brought about, and, optionally, treatment is chronically continued.

26. The method according to claim 2 for treating hypercholesterinemia, wherein the polyene macrolide is chronically administered to the patient in a daily oral dose of about 0.5 to 4 g.

27. The method according to claim 2 for treating prostatic hyperplasia, wherein the polyene macrolide is chronically administered to the patient in a daily dose of about 0.5 to 4 g.

28. The method according to claim 2 for treating gallstones, wherein the polyene macrolide is administered to the patient in a daily dose of about 0.5 to 4 g at least until the gallstones have disappeared, preferably administration is chronic.

29. The method according to claim 2 for treating acne wherein the polyene macrolide formulated into a suitable pharmaceutical composition having an active ingredient content of about 20 to 200 mg/g of the composition is applied several times a day to the affected skin parts and/or the polyene macrolide is administered in a daily oral dose of 0.5 to 4 g until the acne disappears, optionally treatment is chronic.

30. The method according to claim 2 or 3, wherein the polyene macrolide is administered in a daily oral dose of about 1 to 2 g, or is topically applied as a composition having an active ingredient content of about 50 to 100 mg/g of the composition.

31. The method according to any one of claims 1 to 3, wherein the polyene macrolide is nystatin.

32. The method according to claim 3, wherein the polyene macrolide is amphotericin B.

33. A pharmaceutical composition for topical administration, containing a polyene macrolide or a functional derivative thereof in a concentration of about 40 to 200 mg/g of the composition together with usual pharmaceutically acceptable auxiliaries.

34. A pharmaceutical composition for oral administration containing a polyene macrolide or a functional derivative thereof in a dose of about 200 to 500 mg optionally in combination with usual pharmaceutically acceptable auxiliaries.

35. A method for modulating the energy conversion in the body cells of a mammal, comprising the oral administration to the mammal, of at least one polyene macrolide or functional derivative thereof in an amount influencing the frequency of variations in the cellular potential.

36. The method according to claim 2, wherein the polyene macrolide is nystatin.

37. The method according to claim 2, wherein the polyene macrolide is amphotericin B.

* * * * *